United States Patent [19]

Sheehan

[11] Patent Number: 4,535,772

[45] Date of Patent: Aug. 20, 1985

[54] SKIN CLOSURE DEVICE

[75] Inventor: Joseph C. M. Sheehan, Burr Ridge, Ill.

[73] Assignee: Kells Medical, Incorporated, Burr Ridge, Ill.

[21] Appl. No.: 500,854

[22] Filed: Jun. 3, 1983

Related U.S. Application Data

[63] Continuation-in-part of Ser. No. 472,053, Mar. 10, 1983, , which is a continuation-in-part of Ser. No. 367,671, Apr. 12, 1982, abandoned.

[51] Int. Cl.³ .............................................. A61B 17/08
[52] U.S. Cl. ..................................... 128/337; 128/335
[58] Field of Search ................................ 128/325–326, 128/334 R, 335, 337, 346; 227/DIG. 1 B

[56] References Cited

U.S. PATENT DOCUMENTS

| | | |
|---|---|---|
| 655,190 | 8/1900 | Bramson . |
| 1,452,372 | 10/1921 | Gomez .............................. 128/337 |
| 2,421,193 | 8/1943 | Gardner . |
| 2,523,812 | 4/1949 | Carr . |
| 2,811,971 | 11/1971 | Scott . |
| 2,898,741 | 8/1953 | Milliken . |
| 3,516,409 | 6/1970 | Howell . |
| 3,648,705 | 3/1972 | Lary . |
| 3,695,271 | 10/1972 | Chodorow . |
| 3,807,394 | 4/1974 | Attenborough . |
| 3,825,010 | 7/1974 | McDonald ........................ 128/337 |
| 3,831,608 | 8/1974 | Kletschka et al. . |
| 3,863,640 | 2/1975 | Haverstock . |
| 3,933,158 | 1/1976 | Haverstock ....................... 128/335 |
| 3,939,828 | 2/1976 | Mohr et al. . |
| 3,983,878 | 10/1976 | Kawchitch ....................... 128/335 |
| 4,073,298 | 2/1978 | Le Roy . |
| 4,114,624 | 9/1978 | Haverstock . |
| 4,275,813 | 6/1981 | Noiles . |

FOREIGN PATENT DOCUMENTS 477704 5/1976 Australia .
2038038 3/1971 Fed. Rep. of Germany .

Primary Examiner—Stephen C. Pellegrino
Assistant Examiner—Gene B. Kartchner
Attorney, Agent, or Firm—Willian Brinks Olds Hofer Gilson & Lione Ltd.

[57] ABSTRACT

An improved skin closure device is disclosed which includes a pair of attachment members adapted to be positioned along either side of a wound to be closed, wherein the wound is of the type having a denuded region between the marginal edges of the wound. The device includes a plurality of pins associated with the attachment members for the purpose of mechanically securing the attachment members to underlying skin layers, as well as an adhesive interface adapted to adhesively secure the attachment members to the epidermis. A number of interconnecting devices are disclosed which operate to provide a biasing force tending to bring the two attachment members together in order to close the wound gradually and progressively.

20 Claims, 40 Drawing Figures

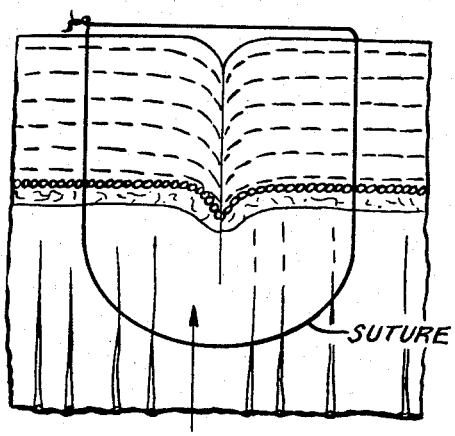
ISCHEMIC
FIG. 3
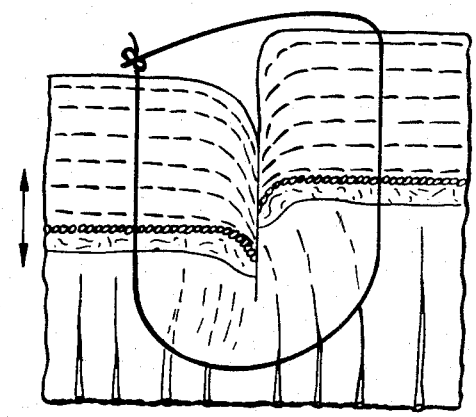
VERTICAL SHIFT
FIG. 3a
FIG. 4
UNEQUAL CENTERING OF STAPLE
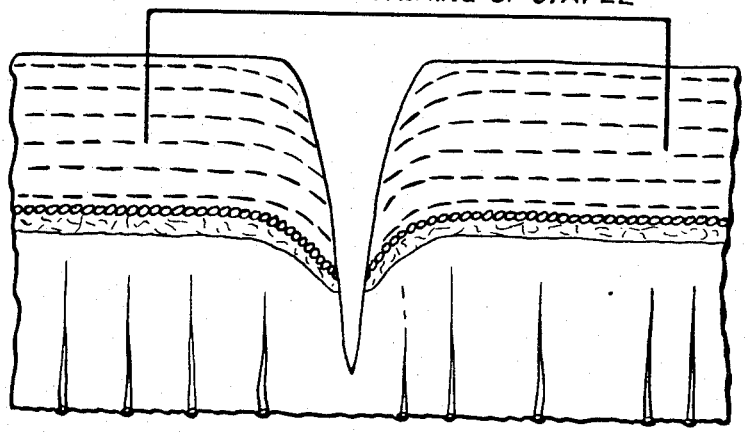
FIG. 4a
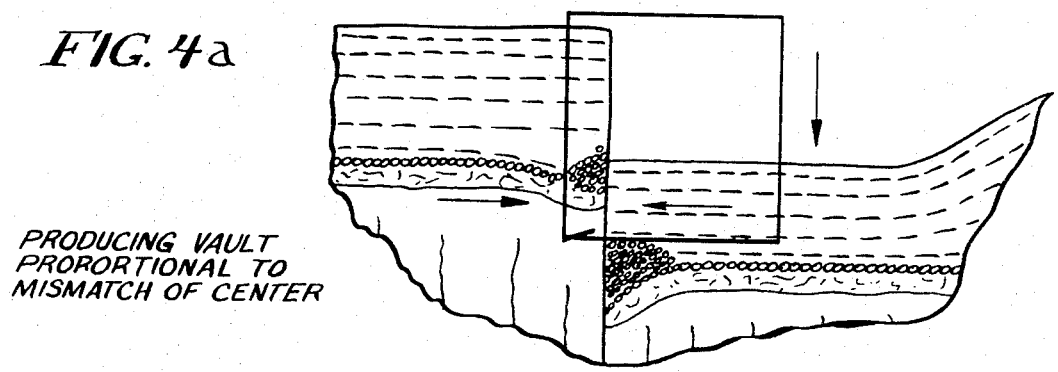
PRODUCING VAULT
PROPORTIONAL TO
MISMATCH OF CENTER

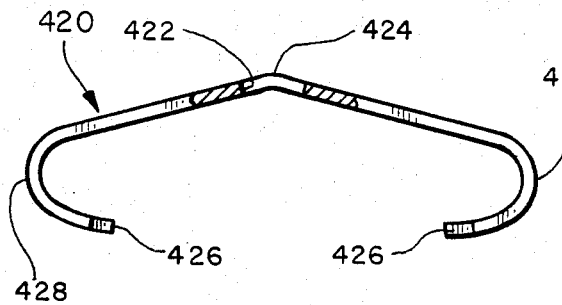
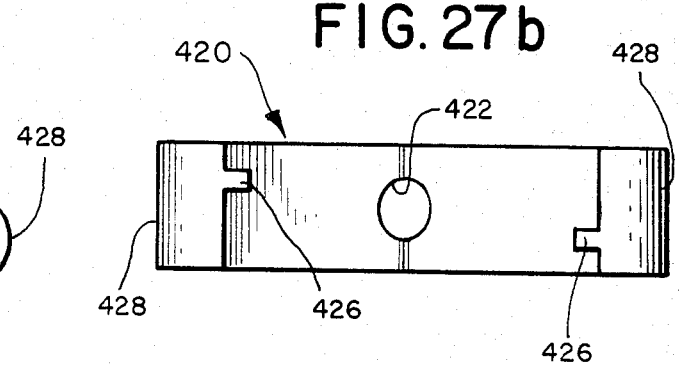
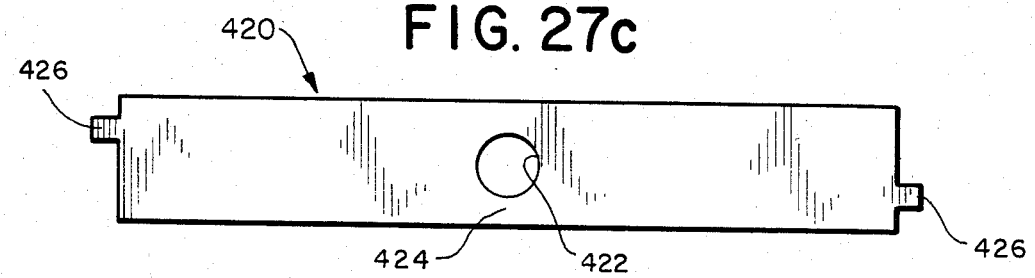
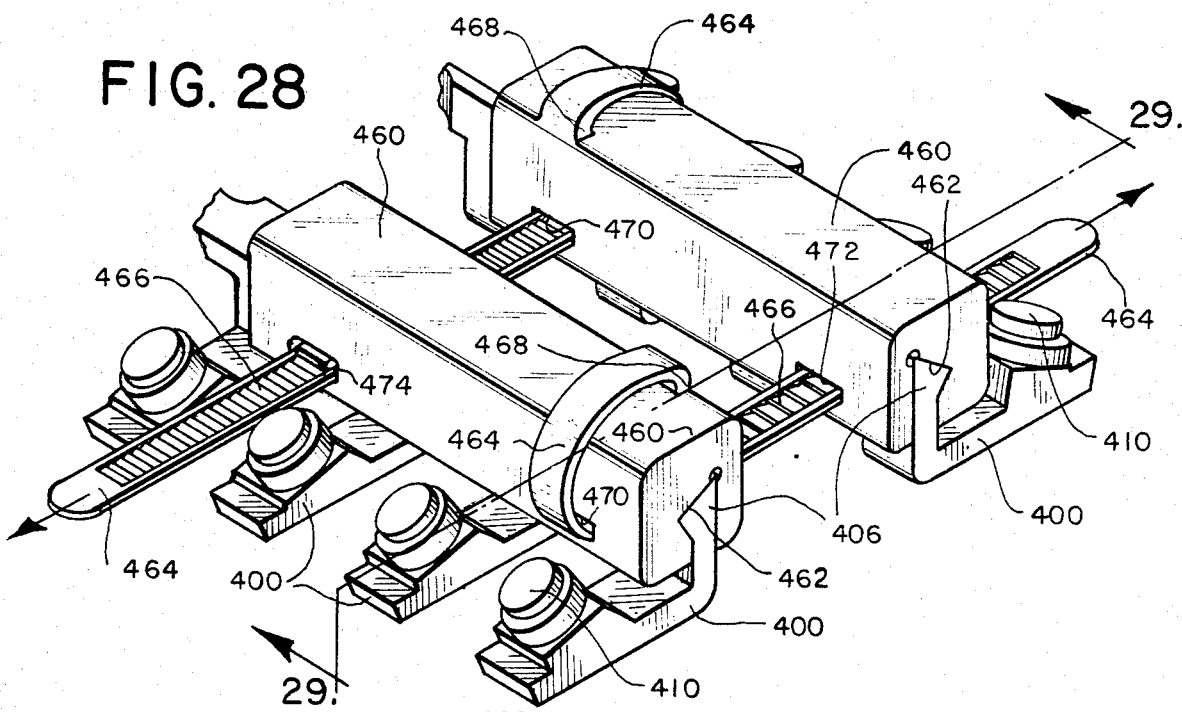
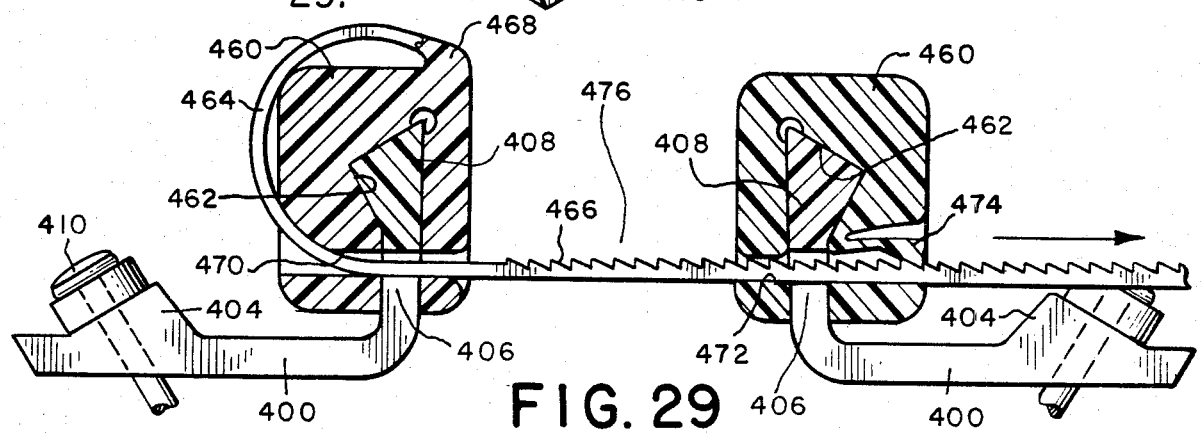

SKIN CLOSURE DEVICE

IDENTIFICATION OF RELATED APPLICATION

This application is a continuation-in-part of co-pending application Ser. No. 06/472,053, filed Mar. 10, 1983, which is in turn a continuation-in-part of co-pending application Ser. No. 367,671, filed Apr. 12, 1982 now abandoned.

FIELD OF THE INVENTION

The present invention relates to an improved skin closure device in the nature of a surgical appliance which is particularly adapted for use in the closure of skin wounds, whether created surgically or by trauma, which device is adapted to gradually close a wound to facilitate the healing process.

BACKGROUND OF THE INVENTION

Conventional surgical practice involves the closure of skin wounds with the use of sutures, clamps, adhesive materials or other similar means.

It is well recognized that skin wounds, whether created by trauma or as a result of surgery, should be closed as soon as possible to avoid contamination and infection, and to minimize the development of scar tissue. The deliberate creation of skin wounds by surgery conventionally requires closure of the wound immediately following the surgery to avoid contamination of the wound and to facilitate repair of the tissue so that the patient may be returned to his normal environment.

Simple suturing of the skin has persisted as a dominant method of skin closure at the present time under a wide range of circumstances. The speed of surgery, however, has developed as an important facet of medical procedure and faster methods for skin closure have been developed, including the use of staples as an accepted method.

In an effort to provide rapid skin closure, a variety of alternatives to sutures and staples have been developed. For example, the following patents disclose various types of brackets which are adhesively affixed to the skin adjacent a wound and are then releasably secured together to close the wound: U.S. Pat. Nos. 4,114,624, 3,933,158, 3,863,640 to Haverstock; U.S. Pat. No. 3,516,909 to Howell; Australian Pat. No. 477,704 to Kawchitch; and West German Pat. No. 2,038,038 to Keil. In addition, the following patents disclose various types of brackets which are affixed to the skin by pins adjacent a wound and are then releasably secured together to close the wound: U.S. Pat. No. 3,825,010 to McDonald and U.S. Pat. No. 4,073,298 to LeRoy. U.S. Pat. No. 1,452,372 to Gomez discloses a skin closure device of the general type discussed above in which both adhesives and pins are used to secure the brackets to the skin.

At the present time, under normal circumstances, there are three generally recognized methods of skin closure. One involves a simple bandaging of the skin with an adhesive material which involves pulling the skin edges together from edge-to-edge with adhesive straps. Another method involves the suturing of wounds through use of a variety of skin suture methods. The third involves skin closure by stapling the skin edges together. In addition, a fourth approach is to use one of the separable brackets discussed above, though the majority of these brackets have not achieved widespread acceptance.

Skin closure is a particular problem when skin must be drawn across a region from which the epidermis and subcutaneous layers are absent in order to close a wound. Such a region will sometimes be called a "denuded area" in the following specification and claims. For example, certain kinds of trauma can bruise, gouge or remove large strips of skin, leaving a wound which is denuded over a significant width. Similarly, after amputation of a limb, a relatively large denuded area is exposed. It would be advantageous to draw skin together from the marginal edges of such a wound in order to bring about speedy closure of the wound. However, this approach has met with considerable difficulty in the past. When sutures are used in an attempt to close such a wound, it is generally not feasible to tighten the sutures progressively as required to close the wound gradually. Similarly, the use of adhesive bandages to bond the superficial layer of the skin and then to pull the superficial layer of the skin on opposite sides of the wound together has also been found unsatisfactory in many cases. Thus, a need exists for an improved means and method of skin closure which will allow skin to be pulled together over a denuded region.

The skin closure devices set forth herein provide significant improvements over the skin closure devices discussed above.

ANATOMY OF THE SKIN

In general, human skin is made up of many separately defined layers, which for simplicity can be grouped in three commonly defined layers. The outer layer is called the epidermis and includes a layer of dead cells which gradually form a pavement network, layer upon layer. This network forms an impermeable boundary of dead or dying cells at the exterior or superficial layer of the skin. These cells are gradually replaced in a continually evolving process as new layers of cells are produced from within.

The second layer to be discussed here is the germinal epithelium, sometimes called the dermis, which is the true growth area of the skin. The germinal epithelium is a relatively thin layer in relation to the other two layers being generally described here. This basement, or germinal epithelium,, is constantly replacing the layer above it and gradually pushing the most superficial layer towards the outside of the skin. The proper joining of this layer is important since this is the layer which, when joined properly end-to-end with a surgical closure device, will give a good or near perfect junction between the dermis on one side of the wound and the dermis of the other side, thereby minimizing the formation of scar tissue. For example, this is the layer which, when burned by deep burns, will often require skin graft. In general, nothing can replace this layer of skin other than germinal epithelium itself, either growing from the side or transplanted when lost.

Beneath the germinal epithelium lies the basement membrane, which is a thin layer of delicate noncellular material of a fine filamentous texture whose principal component is collagen. This layer gives body and support to the overlying germinal epithelium, and is a fatty, fluid-like layer which provides a generally defined cushioning effect whereby the germinal epithelium can easily slide over the muscles. This subcutaneous tissue has poor adherent qualities and poor healing qualities, of itself, since it is of a semifluid character in the normal state and often does not come together well when sutured.

The nature and physical properties of each of the three skin layers generally described above are somewhat different. For example, the outer, crusty layer of stratified epithelium, described as the epidermis, is relatively dehydrated. It generally varies in thickness with the maximum thickness being on the sole of the foot and the minimum thickness being in the facial area. It has the ability to be pulled together and can be joined with an adhesive material to close a wound in the stratified epithelium.

It should be noted, however, that the germinal epithelium and the basement membrane, generally described above, lie at some depth with respect to the epidermis and are critically important to skin closure since they are the primary source of healing with respect to any skin wound.

The basement membrane is made up of high density collagen material which, when cut, has a tendency to recoil and, subsequently, will often result in movement inwards toward the body of the germinal epithelium. The fatty layer beneath offers insufficient resistance to prevent this recoil mechanism and may allow the germinal epithelium to be maintained in a retracted condition over the course of a significant period of time.

SUMMARY OF THE INVENTION

The present invention is directed to improved skin closure devices which to a large extent overcome the problems inherent in the use of sutures, adhesives or stapling means for skin closure, and which provide an environment for rapid healing of the wound.

According to one aspect of this invention, a skin closure device is provided for closing a skin wound which defines first and second wound margins separated by a denuded region. This device comprises first and second attachment members, as well as means for adhesively securing the attachment members to the skin alongside the first and second wound margins, respectively. In addition, means are provided for mechanically securing the first and second attachment members to the skin alongside the first and second wound margins, as for example with pins, staples, or sutures which extend from the respective attachment members into the skin. Means are also provided for interconnecting the first and second attachment members across the wound to adjustably control the separation therebetween in order to allow the separation to be reduced gradually and progressively in order to close the wound gradually.

According to the method of this invention, a skin closure device is provided which includes first and second attachment members and means for interconnecting the first and second attachment members across a skin wound to adjustably control the separation therebetween. The two attachment members are secured to the skin alongside the first and second wound margins, respectively, both mechanically by means of a plurality of pins, staples, sutures, or the like which extend from the attachment members into the skin and adhesively. The interconnecting means is used to bias the two attachment members together in order to tend to close the wound. The interconnecting means is then gradually and progressively shortened in order to draw the attachment members together gradually over the course of several days in order to close the wound gradually.

It has been found that the skin closure method and device of this invention provide surprising advantages in closing skin wounds of the type which include a denuded region from which skin layers are absent. Because the attachment members of the device of this invention are secured to the skin by both adhesive and mechanical means, problems related to differential movement between the epithelium and the dermis are minimized, as are problems related to high localized forces on the skin and resulting damage or tearing of the skin. Furthermore, it has been found that in many cases the method and device of this invention actually stimulate the formation of new skin tissues between the two attachment members as the two attachment members approach each other under the biasing force provided by the interconnecting means. In this way, the speed of healing is increased still further. The skin closure device disclosed below in conjunction with FIG. 25 and following has been found dramatically effective in the closure of wounds around denuded regions. It is effective both in the closing of skin after an amputation, and in the closing of skin after trauma of the sort that extensively bruises, gouges or otherwise removes skin from the wound.

The invention itself, together with further objects and attendant advantages, will best be understood by reference to the following detailed description taken in conjunction with the accompanying drawings.

BRIEF DESCRIPTION OF THE DRAWINGS

FIG. 3 is a schematic representation of a prior art skin closure means involving the use of a suture.

FIG. 3a is a schematic representation of a vertical shift of tissue with a prior art suture closure.

FIG. 4 is a schematic representation of a prior art staple closure for a skin wound.

FIG. 4a is a schematic representation of a vertical shift of tissue as a result of off-center orientation of the staple of FIG. 4 in closure.

FIGS. 27a, 27b and 27c are three views of one of the metal clips included in the embodiment of FIG. 25.

FIG. 28 is a perspective view of two channels suitable for use in a second preferred embodiment of this invention.

FIG. 29 is a sectional view taken along line 29—29 of FIG. 28.

DETAILED DESCRIPTION OF THE PRESENTLY PREFERRED EMBODIMENTS

Turning now to the drawings, FIGS. 25-34 illustrate a number of preferred embodiments of the skin closure device of this invention. As will become apparent from the following discussion, several of these embodiments utilize components shown in other of the drawings in detail and described below. Each of the embodiments of FIGS. 25-34 is suitable for use in closing a wound of the type having a denuded region in which skin tissues are absent between two marginal edges of the wound. These embodiments can be used to draw the marginal skin edges together in order to close the wound gradually and progressively.

Figure 25:
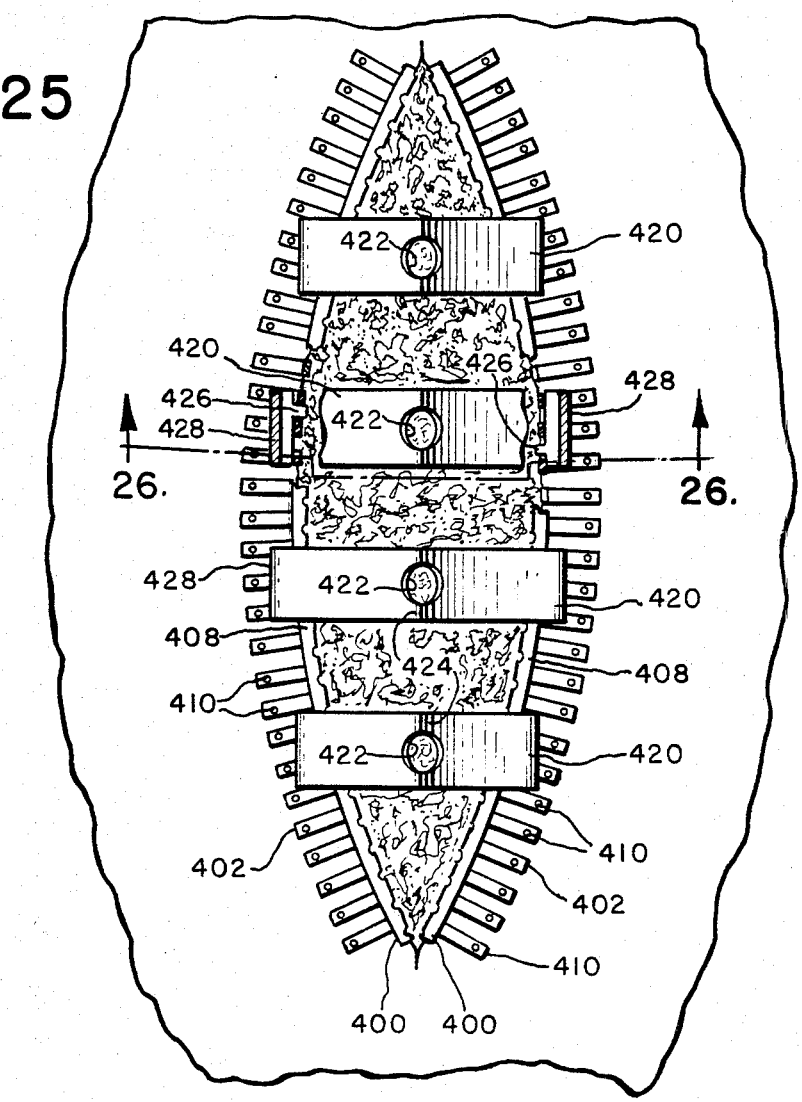
FIG. 25 is a plan view of a first preferred embodiment of the skin closure device of this invention in place adjacent a wound.
Figure 26:
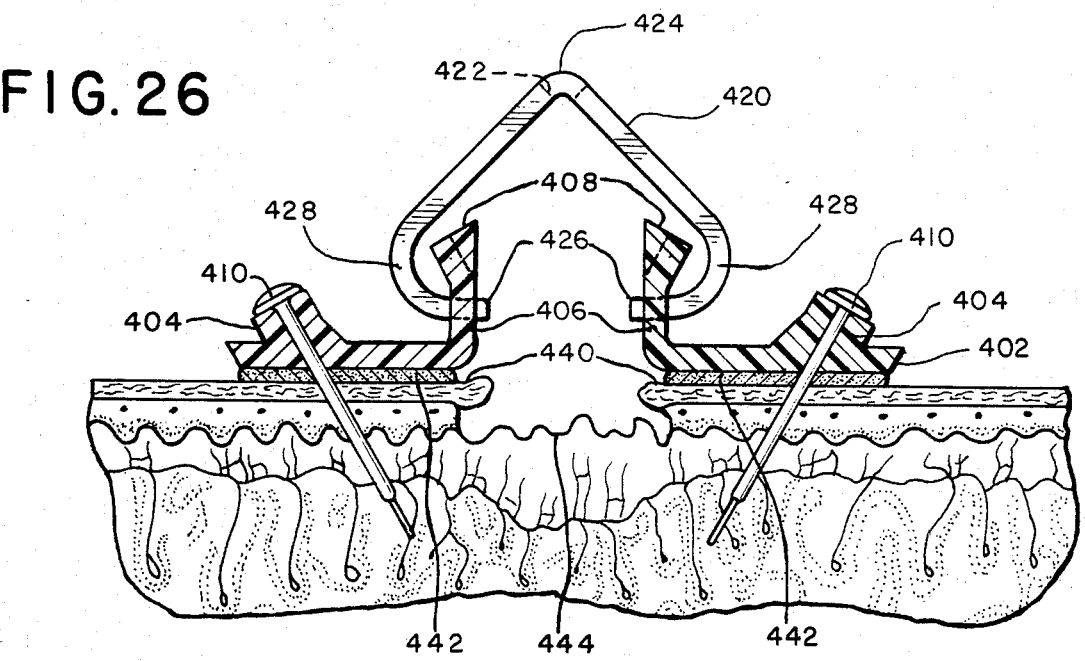
FIG. 26 is a cross-sectional view taken along line 26—26 of FIG. 25.

Turning now to FIGS. 25 and 26, these figures show two views of a first preferred embodiment of the skin closure device of this invention. This embodiment includes two pin harnesses 400, each of which defines a regular array of spaced, parallel, skin contacting members 402. Each of the skin contacting members 402 defines a pin guide 404 near its distal end and is connected at its proximal end to a respective upright member 406. The upper edges of each of the upright members 406 are connected along the length of the pin harness 400 by a rail 408. A plurality of pins 410 are slideably mounted in respective ones of the pin guides 404. The pin harnesses 400 of the embodiment of FIGS. 25 and 26 are described in complete detail below in conjunction with FIGS. 10-13. In this embodiment, each of the pin harnesses 400 is identical to the pin harnesses 110 described in detail below, and each of the pins 410 is identical to the pins 150 described in detail below and shown in FIGS. 10 and 12.

Each of the pin harnesses 400 is secured to a respective marginal edge 440 of a wound. As shown in FIG. 26, a denuded region 444 without skin tissues is disposed between the two marginal edges 440. As described below in conjunction with the embodiment of FIGS. 10-17, the pin harnesses 400 are securely held in place on the marginal edges 440 of the wound both mechanically means of the pins 410 which extend through the epidermis into the dermis, and adhesively by means of a layer of adhesive 442 which secures each of the skin contacting members 402 securely to the epidermis. Thus, the pin harnesses 400 are secured to the epidermis by means of the adhesive layer 442, and they are mechanically engaged with underlying skin layers by means of the pins 410.

As shown in FIGS. 25 and 26, a plurality of clips 420 are provided to interconnect the two pin harnesses 400. Each of these clips 420 is in this preferred embodiment formed of a metal such as aluminum. Each of the clips 420 defines a central aperture 422, as well as a transverse crease 424. The aperture 422 is provided to reduce the bending strength of the clip 420 at the crease 424. Each end of the clip 420 defines a respective projection 426 sized to fit between adjacent upright members 406 of the pin harnesses 400. The projections 426 serve to secure the clips 420 in place on the pin harnesses 400. Finally, each of the clips 420 defines two curved regions 428 disposed between the projections 426 and the crease 424. These curved regions 428 allow the clips 420 to extend around and over the rails 408 of the pin harnesses 400.

FIGS. 27a, 27b and 27c provide three views of one of the clips 420. In the folded configuration of FIGS. 27a and 27b, the overall height of the clip 420 between the crease 424 and the underside of the projection 426 is 0.5 inches. The initial spacing between opposed projections 426 is 1.5 inches, and the overall width of the clip 420 between the curved regions 428 is 2.25 inches. In typical embodiments of this invention, the clip 420 should be suited for interconnecting harnesses 400 on respective sides of a wound having a width of at least one-half inch. FIG. 27c shows a view of a clip 420 before it is bent into the configuration of FIG. 27a. Each of the projections 426 is 0.125 inches in length and 0.0625 inches in width. The width of each of the clips 420 in this embodiment is 0.5 inches, and the diameter of the aperture 422 is 0.1562 inches. In this embodiment, the aluminum from which the clips 420 are formed is 0.049 inches in thickness and the aluminum is type 5052 half hard aluminum.

In use, the embodiment of FIGS. 25-27c is applied to a wound by first adhesively affixing each of the pin harnesses 400 to the marginal edge of the wound, approximately one to two millimeters back from the wound edge. Either local or general anesthesia can be used as appropriate. Once each of the pin harnesses 400 has been adhesively affixed in place, the pins 410 are then pushed into the skin in order to engage the pin harnesses 400 mechanically with deeper layers of the skin. Except for the fact that the pin harnesses 400 are spaced from the wound edge by one to two millimeters, the pin harnesses 400 are secured to the skin using the same procedures as those described below in conjunction with the embodiment of FIGS. 10–17.

Once the harnesses 400 have been secured to the skin, the clips 420 are applied to exert a force tending to bring the two pin harnesses 400 together. A pliers-like tool, such as an allis clamp, can be used for this procedure, and one approach to this procedure is simply to grip the two curved regions 428 between the jaws of an allis clamp and then to squeeze the two curved regions 428 together in order to reduce the effective length of the clip 420 to obtain the desired biasing force. Once the allis clamp is removed from the clip 420, the clip's rigidity tends to maintain it at the desired spacing.

In tightening the clips 420, it is important to provide the correct level of biasing force tending to bring the two harnesses 400 together. If the biasing force is too low, the wound will not close as rapidly as desirable. If the biasing force is too high, excessive forces will be applied to adjacent skin and peripheral circulation will be reduced to an undesirable degree. Generally, it is advisable to tighten the clips 420 to provide an effective biasing force without applying forces to adjacent skin which collapse capilliary vessels. One effective approach is to tighten the clips 420 until adjacent skin turns white, and then to relax the clips until normal circulation and skin color are restored. Skin has a tendency to flow after the harnesses have been biased for a period of about 24 hours, and the clips 420 can be re-tightened at that time to restore the biasing force tending to close the wound.

From this description, it should be apparent that it is preferable to build the clips 420 out of a material such as aluminum which does not relax substantially or allow the pin harnesses 400 to separate from one another once the clamp is released. Preferably, each of the clips 420 is wide enough to distribute contact forces over the pin harnesses 400 to prevent localized bending of the pin harnesses 400.

By progressively bending the clips 420 in order to bring the harnesses 400 closer and closer together, the wound can be closed gradually over a period of days or weeks. For example, a time period of about ten days may be required to close a wound having a denuded area 1.5 inches in width. In order to protect the wound, the pin harnesses 400, and the clips 420 during the healing process, the entire region can be enclosed in a cast which is provided with pockets or windows aligned with the clips 420. The cast protects the clips 420, and yet the clips are reachable through the windows to allow the clips to be progressively bent and tightened. For example, a surgeon can bend each of the clips 420 every other day as appropriate to bring the pin harnesses 400 closer and closer together and thereby to close the wound gradually.

It has been found that the embodiment of FIGS. 25–27c actually works to stimulate movement of subcutaneous tissues ahead of and between the two pin harnesses 400. For example, if the pin harnesses 100 begin at a separation of 1.5 inches, it is not unusual for the entire wound to be closed with a layer of skin by the time the separation between the pin harnesses 400 has been gradually reduced to 0.7 inches. This new skin tissue between the pin harnesses 400 may not be sufficiently smooth for cosmetic purposes; however, it does close the wound and seal it quickly and effectively. If desired, later plastic surgery can be used to improve the cosmetic appearance of the new skin.

Turning now to FIG. 28, a second preferred embodiment of this invention utilizes two channels 460 instead of the clips 420 in order to control the separation between the pin harnesses 400. The embodiment of FIG. 28 is adapted for use with the same pin harnesses 400 as the embodiment of FIG. 25. As shown in FIG. 28, each of the channels 460 defines a respective longitudinal recess 462 sized to receive the rail 408 and upright members 406 of one of the pin harnesses 400. In this embodiment, each of the channels 460 defines a flexible strap 464 which is attached to the channel 460 at an attachment end 468, and which defines an array of saw-tooth shaped teeth 466 along one surface. Each of the channels 460 also defines a guide slot 470 sized to receive the strap 464 and to conduct it between two adjacent upright members 406.

Each of the channels 460 also defines a ratchet guide 472 which includes a pawl 474, as shown in FIG. 29. The ratchet guide 472 and pawl 474 are designed to receive and grip the strap 464 by engaging the teeth 466. The ratchet guide 472 is preferably positioned to guide the strap 464 between two adjacent upright members 406 of the pin harness 400.

FIG. 28 shows the manner in which two of the channels 460 can be used as an interconnecting means to interconnect two pin harnesses 400. When the straps 464 are passed as shown from the guide slot 470 of one channel 460 to the ratchet guide 472 of the other channel 460, a bridging region 476 of the strap 464 is created between the two channels 460. The teeth 466 of the straps 464 are assymetrical and are shaped so as to allow the bridging region 476 to be shortened by pulling on the respective free end of the strap 464, while preventing reverse movement.

The embodiment of FIGS. 28 and 29 can be used in a manner similar to that described above in conjunction with the first preferred embodiment. After the pin harnesses 400 have been installed in the manner described above, the straps 464 are threaded through the ratchet guides 472 and the free ends of the straps 464 are pulled through the ratchet guides 472 in order to reduce the separation between the two channels 460 as desired. By periodically shortening the bridging regions 476, the embodiment of FIGS. 28 and 29 can be used to reduce the separation within the pin harnesses 400 gradually and progressively, and thereby to close the wound. Preferably, the bridging regions 476 of the straps 464 are formed of a plastic material which provides a sufficient amount of elongation under tension such that the straps 464 provide a resilient biasing force tending to close the wound. The embodiment of FIG. 28 provides the advantage that the bridging region 476 of the strap 464 is positioned low and close to the wound. In this way, tipping moments on the pin harnesses 400 are minimized.

Figure 30:
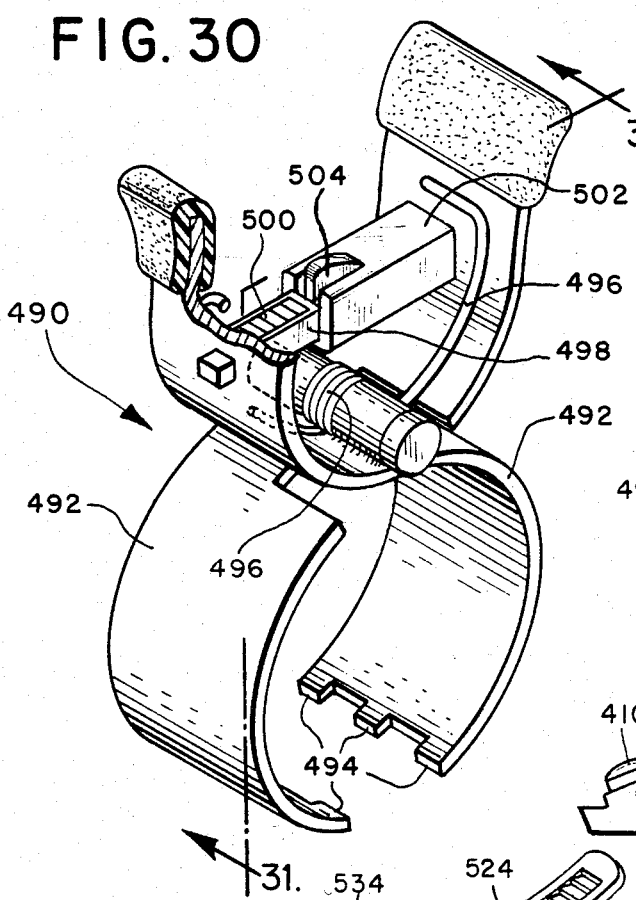
FIG. 30 is a spring clip suitable for use in a third preferred embodiment of this invention.
Figure 31:
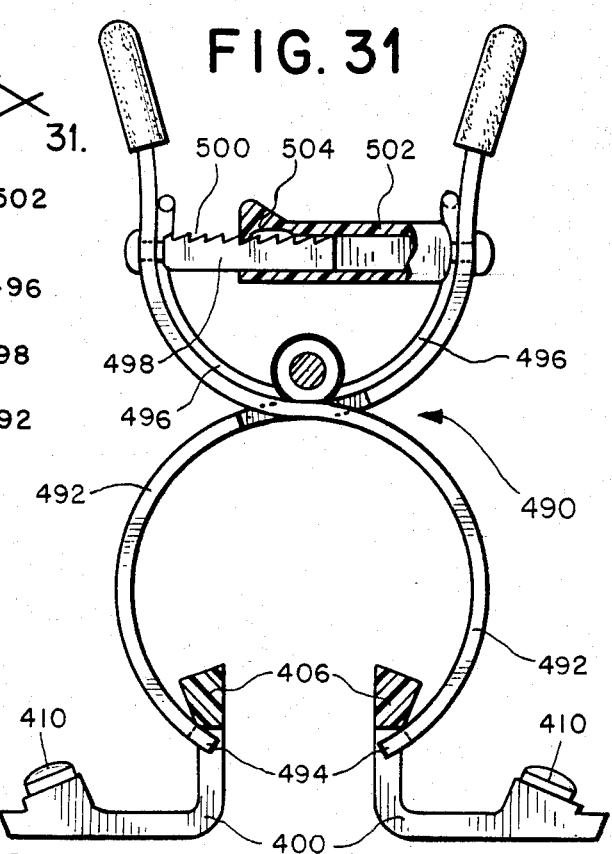
FIG. 31 is a sectional view taken along line 31—31 of FIG. 30.

FIG. 30 shows a third approach to forming an interconnecting means for biasing the two pin harnesses 400 together. As shown in FIG. 29, this approach contemplates a spring clip 490 which defines two opposed jaws 492, each of which defines a plurality of projections 494 sized to fit between adjacent upright members 406 of the pin harnesses 400. The two jaws 492 are hinged about a hinge pin, which serves to mount a spring 496 configured to bias the two jaws 492 together. In this embodiment, a ratchet bar 498 is mounted as shown in FIG. 31 and provided with a regular array of teeth 500. This ratchet bar 498 fits into a ratchet guide 502 which is mounted to the opposed portion of the clamp. This ratchet guide 502 comprises a pawl 504 as shown in FIG. 31. The pawl 504 cooperates with the teeth 500 in order to allow the ratchet bar 498 to be pulled out of the ratchet guide 502, but not to be pushed into it.

In use, the spring clip 490 is used in much the same manner as the clip 420 of FIGS. 25–27c. However, instead of progressively bending the clip 420 to achieve the desired forces, the spring clip 490 serves automatically to provide a resilient biasing force tending to close the wound as the separation between the pin harnesses 400 is reduced. The spring clip 490 is merely applied to the pin harnesses 400 after they have been secured to the skin, and then the spring action of the spring 496 biases the two pin harnesses 400 together. The ratchet bar 498 and ratchet guide 502 ensure that the spring clamp 490 does not allow the pin harnesses 400 to separate from one another, but rather ensures that the separation therebetween is gradually decreased. If necessary, two or more spring clips 490 of varying sizes can be used successively in order to maintain the biasing force tending to close the wound within the desired range as the separation between the pin harnesses 400 is reduced. If desired, the ratchet bar 498 and ratchet guide 502 can be deleted if not needed for certain applications. In an alternative embodiment (not shown) an elastic band may be used instead of the spring clip 420 as a connecting means.

Figure 32:
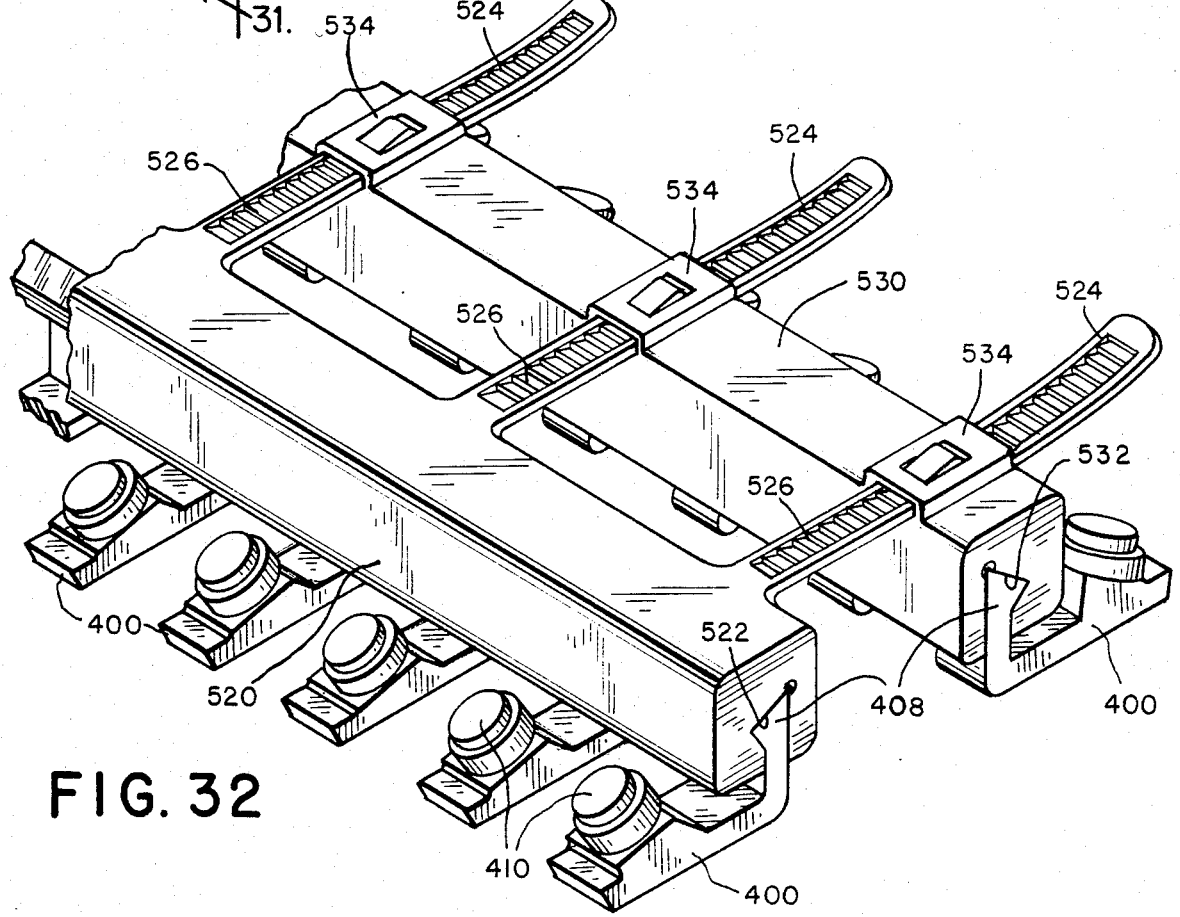
FIG. 32 is a perspective view of a fourth preferred embodiment of the skin closure device of this invention.

Turning now to FIG. 32, a fourth preferred embodiment of this invention provides a strap channel 520 and a ratchet channel 530 for use with the pin harnesses 400 described above. As shown in FIG. 32, the strap channel 520 defines a recess 522 adapted to receive the rail 408 of one of the pin harnesses 400. The strap channel 520 defines a number of straps 524, each of which is provided with an array of assymetrical teeth 526. The ratchet channel 530 similarly defines a recess 532 adapted to receive the rail 408 of the other of the pin harnesses 400. The ratchet channel 530 serves to mount a plurality of ratchet guides 534, each of which is positioned and sized to receive a respective one of the straps 524. Each of the ratchet guides 534 defines a pawl similar to those described above. The ratchet guides 534 cooperate with the straps 524 to permit the straps 524 to be pulled through the guides 534 to reduce the separation between the two channels 520,530, while preventing the separation from increasing. This embodiment is used in a manner similar to that described above in order to reduce the separation between the channels 520,530 gradually and progressively, and thereby to close the skin wound progressively.

Figure 33:
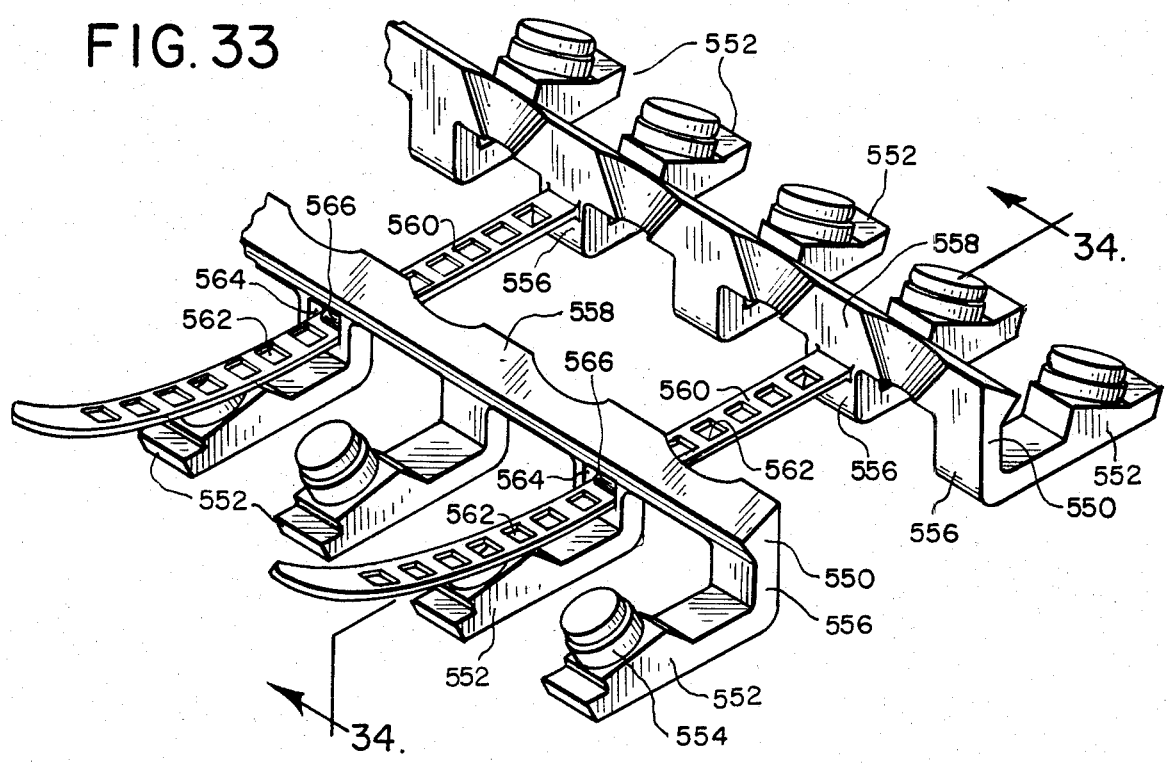
FIG. 33 is a perspective view of a fifth preferred embodiment of the skin closure device of this invention.
Figure 34:
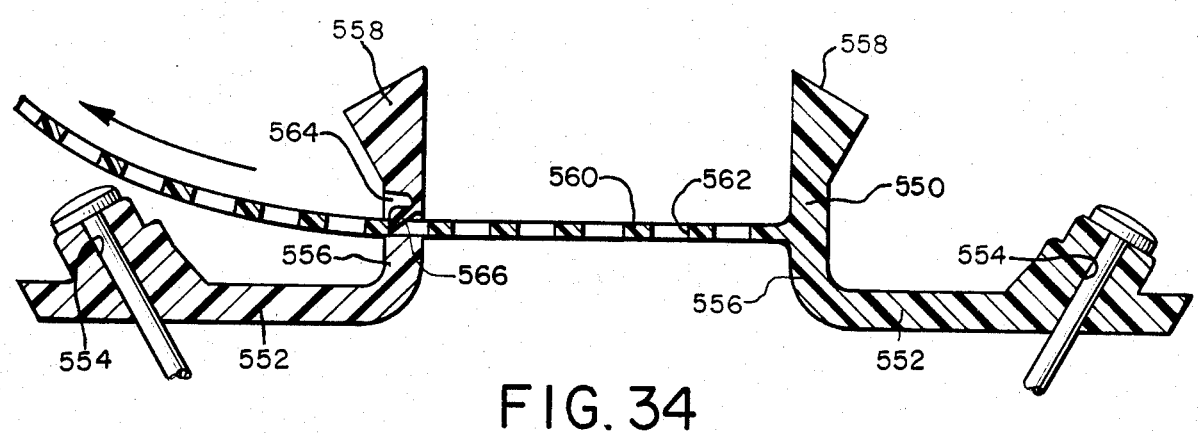
FIG. 34 is a sectional view taken along line 34—34 of FIG. 33.

It should be understood that the present invention can be embodied in skin closure devices which do not utilize the pin harnesses 400 described above. Rather, the pin harnesses can be modified to incorporate the interconnecting means as an integral part thereof. FIG. 33 and 34 show such a device.

As shown in FIGS. 33 and 34, two pin harnesses 550 are provided, each of which defines an array of skin contacting members 552. Each of the skin contacting members 552 defines a respective pin guide 554 similar to that described above in conjunction with the pin harnesses 400. Similarly, each of the skin contacting members 552 terminates at its proximal end at an upright member 556, and the upright members 556 are joined together by a longitudinally extending rail 558. The skin contacting members 552, the pin guides 554, the upright members 556, and the rails 558 can be similar to corresponding elements of the pin harnesses 400.

The embodiment of FIGS. 33 and 34 differs, however, from the pin harnesses 400 in that one of the pin harnesses 550 defines a pair of strips 560, each of which is secured to a respective one of the upright members 556. Each of the straps 560 extends transversely to the rail 558 and is provided with an array of holes 562 extending along the length of the strap 560. The other of the two pin harnesses 550 defines a pair of ratchet guides 564 positioned and adapted to receive respective ones of the straps 560. Each of the ratchet guides 564 defines a respective pawl 566 as shown in FIG. 34, and the pawls 566 cooperate with the holes 562 to provide a one-way action such that the straps 560 can be pulled through the guides 564 to reduce the separation between the rails 558, but cannot be moved in the reverse direction. As before, the straps 560 are preferably formed of a material which provides a degree of resilience when placed in tension, such that the straps 560 provide a resilient biasing force tending to close the wound. The embodiment of FIGS. 33 and 34 can be used in a manner similar to that described above in order to shorten the effective length of the straps 560 gradually and progressively in order to close the wound.

The preferred embodiments described above in conjunction with FIGS. 25–34 provide important advantages in use. First, the pin harnesses are secured to the skin both adhesively to the epidermis and mechanically to underlying skin layers. Because of this compound adhesive/mechanical attachment of the pin harnesses to the skin, it has been found that the pin harnesses can be used to close large skin openings progressively, without pulling the pin harnesses out of the skin or causing extensive damage to the skin. The pins ensure that forces applied to the pin harnesses to close the wound are transmitted to underlying skin layers. In this way, undesirable differential movement between the epidermis and underlying skin layers is avoided. Furthermore, the adhesive bonding layer cooperates with the relatively large number of pins to spread forces applied to the pin harnesses over a relatively large skin area, thereby reducing the tendency of the pin harnesses to be pulled through the skin. Thus, the mechanical and adhesive bonding of the pin harnesses to the skin cooperate to provide a skin closure device with marked advantages.

Of course, it should be understood that a wide range of changes and modifications to the preferred embodiments described above will be apparent to those skilled in the art. The following discussion of FIGS. 1–24 is provided to illustrate in greater detail certain of the structures described above, as well as to illustrate alternative structures for mechanically and adhesively securing an attachment member to the skin. For example, alternative embodiments of this invention may utilize plates which are affixed to the skin adhesively as well as by staples or sutures. These plates may then be biased together by any of the connecting means described above. It is, therefore, intended that the foregoing detailed description be regarded as illustrative rather than limiting, and that it be understood that it is the following claims, including all equivalents, which are intended to define the scope of this invention.

PRIOR ART SKIN CLOSURE DEVICES

Figure 1:
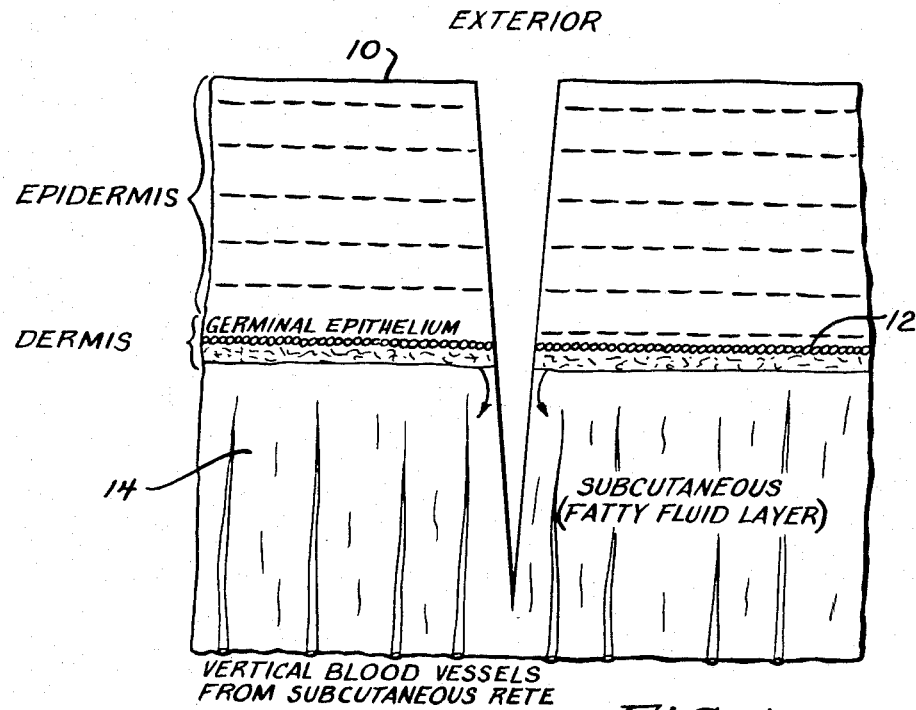
FIG. 1 is a schematic representation of skin tissue defining a wound therein which may be closed by devices of the type disclosed herein.

Referring specifically to FIG. 1 of the drawings, it should be noted that this drawing is a schematic representation of the skin, which, as described above, is made up of many layers. For simplification, these layers can be grouped into three layers with the outer layer being called the epidermis as indicated at 10 in FIG. 1. As noted above, the epidermis 10 defines the outer skin layer and forms an impermeable boundary made up of a network of dying or dead cells.

The basement, or germinal epithelium 12 defines the cell growth area where the growth of cells by multiplication and division replaces the layer above it and gradually pushes the most superficial layer towards the outside of the skin. This germinal epithelium 12 is called the dermis and is the true growth area of the skin. This, it should be noted, is one of the main skin layers involved in the healing process, since this is the layer which, when joined properly in an end-to-end relationship, will provide for optimal healing conditions and for minimal development of scar tissue.

The skin layer lying beneath the germinal epithelium or dermis 12 is the basement membrane 14 which, as noted above, is a thin layer of delicate noncellular material of a fine filamentous texture whose principal component is collagen. The subcutaneous tissue is fatty and fluid-like and gives a cushioning effect so that the dermis 12 can slide easily over the muscles. It should be noted that this subcutaneous tissue has a poor adherent quality, or poor healing quality, since it is in a semi-fluid condition in its normal state and generally does not come together well when sutured.

Figure 2:
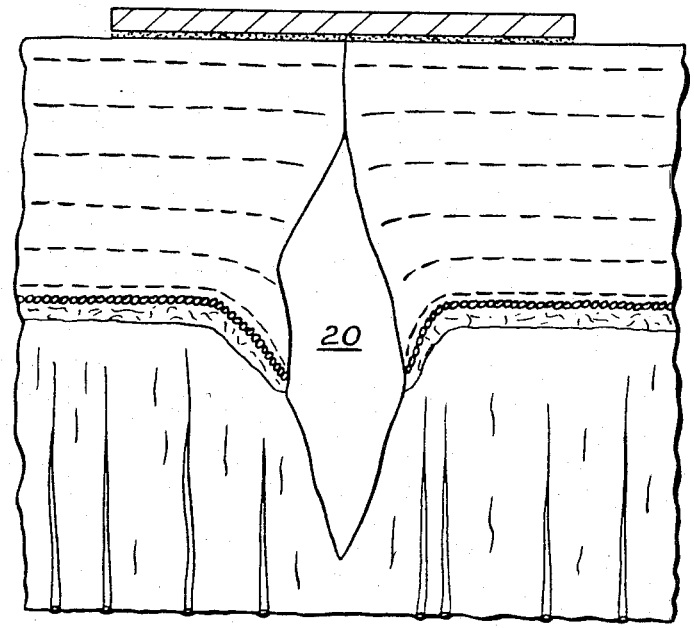
FIG. 2 is a schematic representation of a prior art skin closure device involving the use of an adhesive material.

Referring now to FIG. 2 of the drawings, this figure shows an illustrative example of one of three common methods of skin closure of the prior art, notably, closure of a skin wound with an adhesive material. With reference to the foregoing description of the various layers of dermis, epidermis and subcutaneous tissue, it can be seen that an adhesive layer of the type shown in FIG. 2 brings only the outer border of the epidermis together. In many cases this type of skin closure device does not bring the deep layer of the dermis together, in view of the fact that this device does not come into contact with the dermis in any physical manner. Accordingly, an adhesive skin closure device serves primarily as a dressing to prevent bacterial contamination but does not completely control the recoil of the dermis which can result in the creation of a space, or void. Such a void usually is filled by a hemorrhage clot or some serious clot of seepage of the normal tissue fluids into this area as seen at 20 of FIG. 2. Such a clot 20 will in general eventually coagulate to define a stiffened network across which the dermis eventually will grow in an irregular manner until the dermis is complete. However, such a growth pattern of the dermis often results in a skin irregular underlying basement membrane and an inherent defect which will sometimes persist as an irregularity for the remainder of the life of the patient. It can readily be seen that the use of an adhesive closure, by itself, may result in significant cosmetic problems related to the formation of a permanent, undesirable scar.

Another prior art method of wound closure, schematically represented in FIG. 3, is the suture means of closure. It should be recognized that there are many forms of sutures and suture materials available for the closure of wounds. It is recognized that it is often preferable to use a non-reactive material rather than an absorbable material for sutures, since absorbable sutures will often produce a tissue reaction around the suture, giving rise to scar formation to an extent greater than that which may be cosmetically acceptable to a patient.

Suturing generally is more acceptable in certain areas, such as in the facial area, where the epidermis is of a minimum thickness. Under these circumstances, the suture line on the superficial surface of the skin tends to keep the skin aligned in generally parallel layers, thereby closing the dead space beneath the epidermis to bring the recoiled edges of the dermis into a closely aligned relationship. Such a closure generally will give an acceptable scar tissue for cosmetic purposes. However, such a closure is to some extent unpredictable and to some extent the quality of the closure depends upon the depth of the epidermis. In general, the thinner the epidermis, the greater the probability of getting the dermis properly aligned. A greater depth of tissue can make it difficult to achieve proper alignment, and consequent misalignment of the dermis can result in the development of unacceptable scar tissue. That is, a vertical shift of one layer of epidermis with respect to the other in a "step" fashion (as shown, for example, in FIG. 3a), will result in misalignment of the basement membranes which can eventually result in a widened scar tissue that generally is cosmetically undesirable.

A third commonly employed prior art method for closure of a wound involves the use of staples (as in FIG. 4). This closure method involves little improvement in the avoidance of scar tissue formation, and stapling can be a less predictable means for closure of a wound since every staple is individually inserted into the skin.

Generally, the skin is held everted as the staple is applied across the wound edge, and the staple, when inserted, compresses the wound with the hope that the everted edges will provide the desired alignment. This is a relatively imprecise method of obtaining the desired alignment of the basement membrane of the skin since there is little control over the membrane itself during the closure procedure. As a result, there is a significant change of misalignment, and a resulting vertical shift can result in a less satisfactory wound closure than the simple suture. FIG. 4a illustrates such a vertical shift.

Staples of the type shown in FIG. 4 provide the advantage that they substantially speed the time of closure. In some instances, staples are preferable to simple suturing where the speed of surgery is an element in treatment of the patient. It should be noted, however, that unless the staple is properly placed in the center of the wound upon closure, a vertical defect is often created which is greater when the staple is placed more off-center with respect to the wound. (See FIGS. 4 and 4a.)

SKIN CLOSURE DEVICES RELATED TO THE PRESENT INVENTION

Turning now to FIGS. 5-9a, FIG. 5 is a schematic representation, in section, of a first preferred embodiment. This embodiment is a skin closure device which, to a large extent, overcomes problems inherent in the use of adhesive, suturing or stapling means for skin closure. This embodiment provides a more exacting method of skin closure which minimizes the time needed to close a wound as well as the formation of scar tissue.

It should be noted that an important advantage of the skin closure device of FIGS. 5-9a is that it allows the basement membrane of the skin to be aligned properly. This is a significant factor in the reduction of the production of scar tissue and results in a more cosmetically acceptable wound closure.

The speed of a wound closure is an important factor, since in many instances decreased operating time is highly desirable to reduce the anesthetic risk and to reduce the incidence of bacterial contamination which might occur in a prolonged operation. The improved closure device of FIGS. 5-9a provides the further important advantage of extremely rapid skin closure.

Another desirable feature of the embodiment of FIGS. 5-9a is its versatility in that this embodiment allows the transfixing pins to be removed individually at the surgeon's discretion without the removal of the entire apparatus. This approach leaves the apparatus intact while still allowing for the early removal of pins as may be appropriate and indicated in certain rapidly healing areas such as the face, head and neck.

The device shown in FIGS. 5-9a overcomes to a large extent the problems discussed above through the use of laterally extending plates which are anchored with respect to the wound through a combination of pins extending along the outside edges of said plates and an adhesive which secures the plates to the epidermis and isolates the pins with respect to the skin to avoid movement of the pins which could give rise to tissue damage.

The pins utilized in the embodiment of FIGS. 5-9a may be formed of stainless steel, chrome, cobalt or titanium alloys, or some other suitable nonreactive rigid material.

The ease of application of the present device with respect to the wound permits its use in a wide range of elective surgical procedures without the need to change traditional methods of skin and wound preparation.

Figure 5:
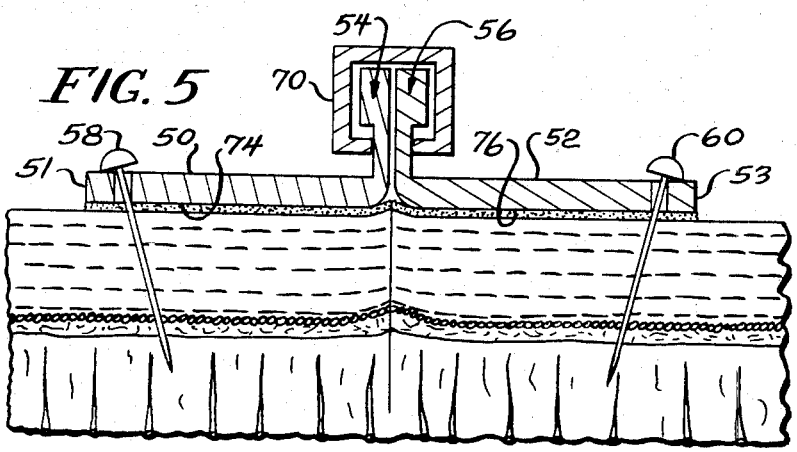
FIG. 5 is a cross sectional elevation of a first preferred embodiment of a novel skin closure device.

For example, when used in a surgical procedure, the closure device of FIGS. 5-9a may first be placed so that the inner abutting portions of the laterally spaced plates extend along the area to be incised. The closure housing is then removed from the device and the incision then may be made in the region defined between the abutting inner plate portions. It can readily be seen that accurate re-alignment of the incised tissue can quickly be realised by bringing the plates back together in an abutting relation and placing the closure housing over the upstanding legs of the plates to hold the plates in assembled relation as schematically represented in FIG. 5 of the drawings.

To obtain proper wound healing, it is important to bring the epidermis, the dermis, as well as the outer layers of the subcutaneous tissue into close apposition and to maintain this orientation during the healing process. This maintenance of orientation is easily obtained with the apparatus of FIGS. 5-9a, and a skin wound can be closed extremely rapidly.

Preferably, all of the materials employed in the making of the device of FIGS. 5-9a are non-reactive with respect to human tissue and, subsequently, minimum scar formation will result from the use of this device.

The apparatus of FIGS. 5-9a includes a pair of spaced apart plate elements 50 and 52. Each of these plate elements includes a plurality of horizontally extending legs shown at 51 and 53 in FIG. 5, each extending laterally into a respective upstanding leg element 54 and 56.

Figure 6:
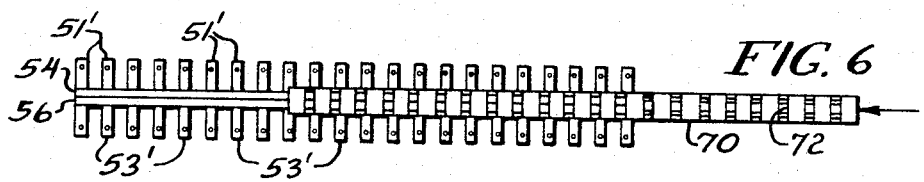
FIG. 6 is a top plan view of the device of FIG. 5 showing the lateral plate assembly and closure housing in partially assembled relation.
Figure 7:
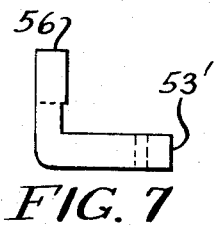
FIG. 7 is an end view of the one of the lateral plate elements of the assembly of FIG. 5.
Figure 8:
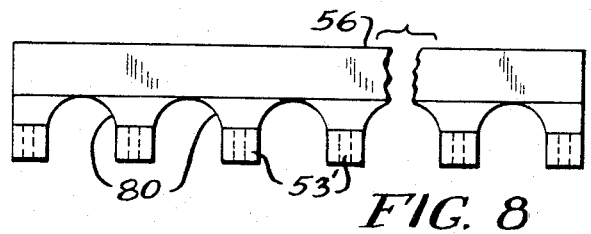
FIG. 8 is a segmented side view of the plate element of FIG. 7.

The general configuration of the plates may readily be seen in FIGS. 6, 7 and 8. The legs 51 and 53 are shaped as a series of spaced apart, projecting, finger-like elements 51 and 53 extending in spaced apart relation along the length of the plate sections.

Each of the spaced apart finger-like elements 51 and 53 of the plates 50 and 52, respectively, is provided with a pin as shown at 58 and 60, extending through the outer terminal portion of the finger-like elements.

Figure 5A:
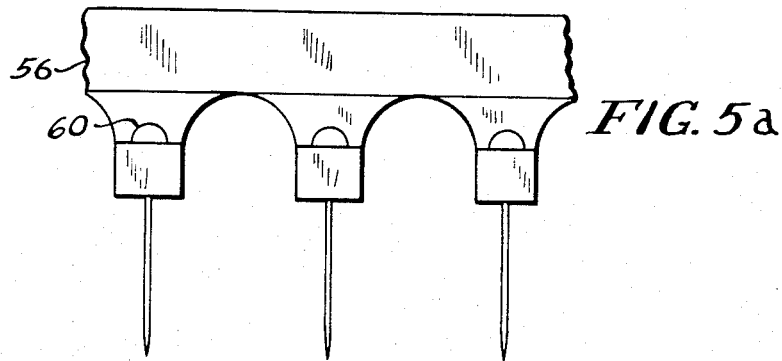
FIG. 5a is a partial side elevation of the device of FIG. 5.

It should be noted that various wound closures may require different closure forces and it may not be necessary to include a pin at the outer terminal portion of each finger-like element. For purposes of illustration the pins are included at said outer terminal portions in FIGS. 5, 5a and 6.

The skin penetration portion of the pins is provided with a beveled terminal portion for the purposes to be noted hereinbelow.

The upstanding portions 54 and 56 of the plates 50 and 52, respectively, include an enlarged portion at the upper terminals thereof to cooperatively associate with a closure housing 70 which will hold the upstanding portions 54 and 56 of the plates 50 and 52 in abutting relation. The housing 70, therefore, will serve to hold the entire closure device in fully assembled configuration to accomplish wound closure in association with the holding forces of the pins, which extend into the tissue, and an adhesive, which bonds the plates 50, 52 to the epidermis. It also should be noted that the housing 70 holds the assembled structure in a fixed orientation to avoid vertical misalignment of the plates 50 and 52 in use.

The adhesive layer is provided along the bottom portions 74 and 76 of the laterally extending portions of the legs of the plates 50 and 52. This adhesive layer is applied to the bottom surface of the plates of the apparatus to maintain the plates in a firmly anchored orientation with respect to the epidermis. The adhesive layer controls any lateral motion of the epidermis and it secures the apparatus to the epidermis, thereby bringing the epidermis in a desired, edge-to-edge, closed configuration.

The laterally extending legs of the plates, as defined by the spaced apart finger-like elements, are made sufficiently wide to spread the distribution of closure forces over a wide area, thereby reducing scar formation which otherwise might have occurred with the use of a stitch, suture or staple that might lie on the skin for a prolonged period. It generally is recognized that the healing process may take anywhere from ten to fourteen days. Sutures or staples which remain in contact with the skin during this process can give rise to skin irritation.

The pins 58 and 60 are preferably provided with a knife-like edge to allow the pins to cut the skin during insertion. This cutting action is preferable to the press fitting action characteristic of use of a regular safety pin, or the like. The sharpened edge of the pins 58, 60 is preferably provided with an acute angle of at least 60 degrees which produces a sharp linear cut in the skin upon insertion of the pin. In this way, scar production by the pins 58, 60 is minimized. This knife-like cutting edge on the pins 58, 60 provides significant advantages.

The pins 58 and 60 may be formed such that they extend slightly inwardly toward the central part of the device as shown in FIG. 5 to provide enhanced wound closure forces. This inward pitch may preferably be on the order of about 15 degrees.

The pins are preferably formed of a high-grade stainless surgical steel which is non-reactive to the body and which will produce no significant soft tissue reaction around it which might be detrimental in the production of scar tissue.

The laterally extending plates 51 and 53, which in the embodiment of FIGS. 5-9a are defined by spaced apart finger-like elements, are integrally attached to the upstanding legs 54 and 56, respectively. The inward portions of the plates 51 and 53 at the portion of attachment to the upstanding legs 54 and 56, respectively, define a radius of curvature which is provided to allow the skin to be everted during the healing process. This eversion of the skin is highly controlled by the shape of the curve joining the laterally extending and upstanding leg portions of the plates 50 and 52 and permits a slight movement of the inboard portion of the plates in relation to the wound being controlled by the assembly. This action in cooperation with the action of the pins 58, 60 controls, via the vertex of the wound, the deeper dermis and tends to neutralize the inversion effect or recoil of the basement membrane during the healing process. The result is that a straight epithilial membrane is defined in end-to-end relationship which often will produce almost no void or vertical step in the depths of the wound.

Figure 9:
FIG. 9 is an end view of the closure housing included in the assembly of FIG. 6.
Figure 9A:
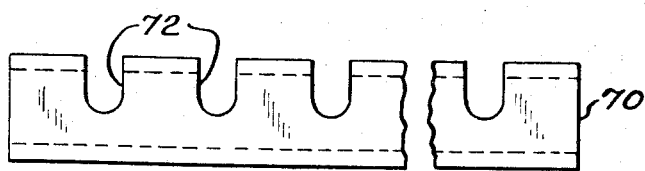
FIG. 9a is a segmented side elevation of the housing of FIG. 9.

The closure housing 70, when in place, locks the two plate elements 50 and 52 in assembled relation and prevents overriding or vertical motion of one side of the wound with respect to other, thereby maintaining proper alignment of the closure. The housing member 70 may be serrated as shown in FIG. 9a of the drawings with the serrations being defined by the cutout sections 72 spaced therealong to provide for flexibility of the assembled apparatus and to allow for free drainage from between the upstanding legs of the plates. In use, the closure housing 70 is positioned in place over the upstanding legs 54 and 56 to define means for rapid approximation of each skin edge being controlled by the apparatus, whether the apparatus is applied after the wound was created or the apparatus is applied prior to the incision of the wound.

The pins 58, 60 are individually pushed into the skin through the pre-formed openings of the finger elements of the plates. A multiple pin insertion apparatus can be provided for this purpose which requires a minimum amount of force to be exerted at the skin edge upon insertion of the pins. It should be noted that, in the preferred embodiment of FIGS. 5-9a, the pins have not been incorporated or molded into the apparatus. This allows the surgeon to remove the pins individually or in groups in accordance with defined surgical procedures. The pins are provided with a safety head on them to prevent migration of the pin into the depth of the wound and also to allow for easy removal of the pin with a simple forceps action, thereby leading the plate adherent to the skin to maintain the wound in an essentially controlled manner once the serous clot and early epithelization has occurred but before full strength has been obtained.

It should be noted that in the preferred embodiment of FIGS. 5-9a suitable drainage sites are provided via the recessed portions 80 (FIG. 8) extending in spaced apart relation along the base of the conjunction of the laterally extending legs 51 and 53 and upstanding leg portions 54 and 56. These drainage sites 80 allow for free drainage to occur from the wound and for the removal laterally of the wound of any excess serous secretion that may build up at the wound edges or to accommodate any hematoma that may build up and tend to lift the apparatus which would subsequently result in discharge of material from the drainage sites 80.

It also should be noted that the drainage sites allow for easy examination of the wound edges to insure that the wound has been carefully brought in apposition and has not been left excessively everted or distracted by the application of the apparatus.

It should be noted that blood is supplied to the skin via a reticular network which is a vertically oriented system. The apparatus of FIGS. 5-9a, unlike sutures or the like, does not interfere or put under compression the skin edges and allows for normal postoperative swelling to occur and recede without interfering with the blood supply to the vital healing tissue. This is an important aspect of the embodiment of FIGS. 5-9a and is a characteristic of the design and use of this apparatus in assembled relation in holding the wound in a closed orientation during the healing process.

It can readily be seen that the laterally extending plate elements 50 and 52 and the closure means may be of any desired length and are made of material which may readily be cut with any convenient apparatus to the exact length desired by the physician or surgeon.

In one preferred embodiment of the device of FIGS. 5-9a, the plates and closure housing are made of nylon which in its characteristic form will have sufficient flexibility in use, so that the apparatus may be placed in a lateral spaced apart configuration with respect to the wound in any desired configuration and made to adapt the characteristic nature of the wound. This flexibility characteristic is, of course, enhanced in the preferred embodiment of FIGS. 5-9a by the use of the spaced apart finger-like projections on the laterally extending plate elements 51 and 53 and the drainage site serrations 80 associated therewith. The removal of this material, of course, permits increased flexibility of the apparatus for convenience in use. It should be noted, however, that a material which is too flexible may defeat the purpose of the apparatus if the material is not sufficiently rigid to maintain the wound closure in proper orientation Therefore, it is important to provide the degree with a proper degree of flexibility which permits a preferred orientation of the device with respect to the wound while still being sufficiently rigid to hold the wound in the desired close orientation during the healing process.

During the application procedure it should be noted that the pins are in a fully retracted position and do not extend substantially below the lower face of the laterally extending segments 51 and 53. This permits initial application in the non-penetrating area of the skin without the need for holding the skin edges with a forceps and further traumatizing the delicate skin edges. It should be noted that the undersides of the laterally extending plate elements 51 and 53 are provided with the adhesive interface which will orient the plate elements with respect to the skin. Accordingly, the apparatus can be put on atraumatically and closed without any forceps touching the skin edge. Further, the adhesive layer on the underside of the laterally extending plate elements is such that if the element is applied in an unsatisfactory orientation it can easily be removed and reapplied in the proper orientation of the plate elements 50 and 52 with respect to the wound. The pins may be inserted individually or in groups to provide a rapid rate of closure which is substantially in excess of commonly used suturing techniques and which may even be faster than the application of staples for wound closure. Since there is substantially no motion between the pins which transfix the skin and the surrounding skin (a feature provided by the adhesive interface associated with the plate), there is substantially no motion of the skin at the site of the pins. The adhesive interface closes the skin puncture at the pin to bacterial contamination over the course of the healing process and also reduces the motion of the pins which could result in the production of scar tissue. It has been my experience that this combination of pins and adhesive along with the sharp pin knife edge produces an atraumatic and almost scarless pin site.

The apparatus of FIGS. 5–9a can be applied either after the wound has been created at the time of surgery or before the skin is cut and then subsequently separated at the time of the surgical incision. This latter approach minimizes the time required to close the wound. It also should be noted that the removal of the apparatus from the skin can occur in two ways: the pins can be removed one at a time at the time of healing, or alternately one edge of the apparatus can be lifted and peeled off. There is little pain involved in this maneuver since the pins are typically in place for a period of more than forty-eight hours, and removal of the pins in such a manner will typically not cause patient discomfort. Patient discomfort in the removal of sutures or staples can be greater since staples tend to catch the patient on the deep elbow as they are removed.

Turning now to FIGS. 10 through 24, a number of alternative embodiments will be discussed in detail. In these drawings, FIGS. 10 through 19 disclose a second preferred embodiment which is in many ways similar to the first preferred embodiment described above. FIGS. 20 through 24 disclose three additional embodiments which differ significantly from the first two embodiments in important respects. In FIGS. 10 and 21–24, the reference numeral 350 has been used to designate a skin wound, the reference numeral 352 has been used to designate superficial skin layers (the epidermis), the reference numeral 354 has been used to designate the dermis, and reference numeral 356 has been used to designate the marginal edge of the skin wound.

Figure 10:
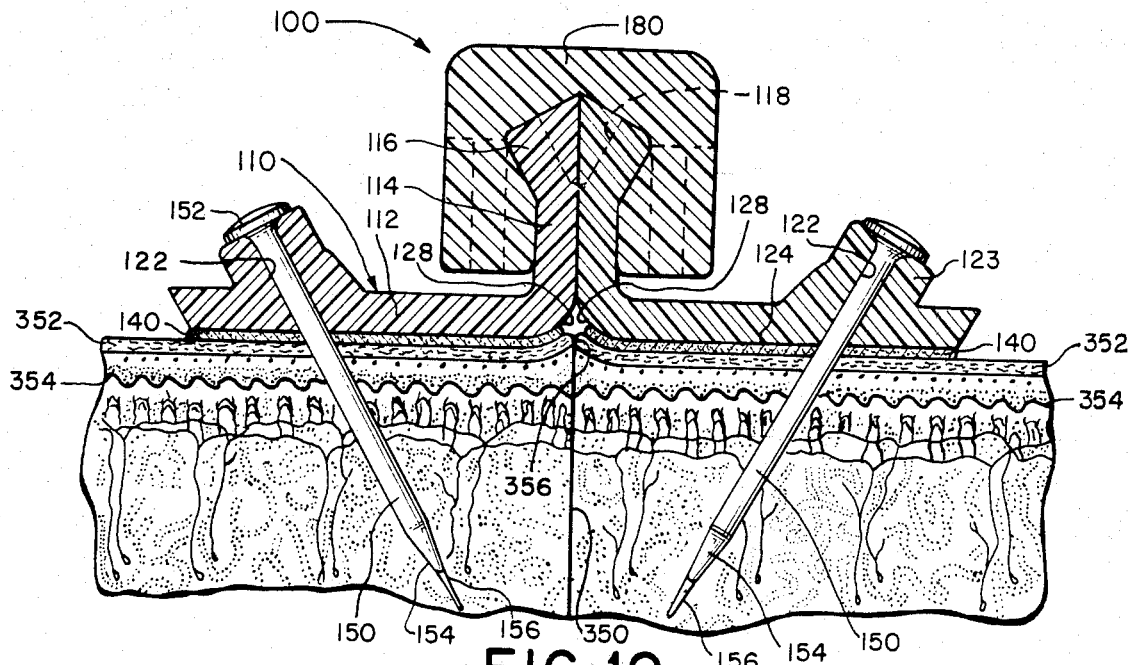
FIG. 10 is a cross-sectional elevational view of a second preferred embodiment of novel skin closure device.
Figure 11:
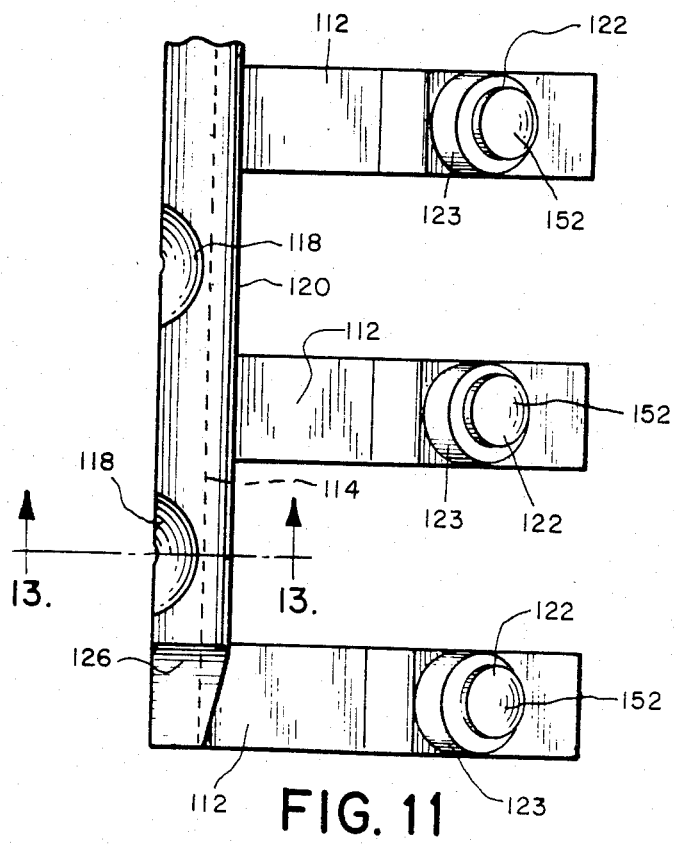
FIG. 11 is a top plan view of a portion of one of the pin harnesses of the embodiment of FIG. 10.
Figure 12:
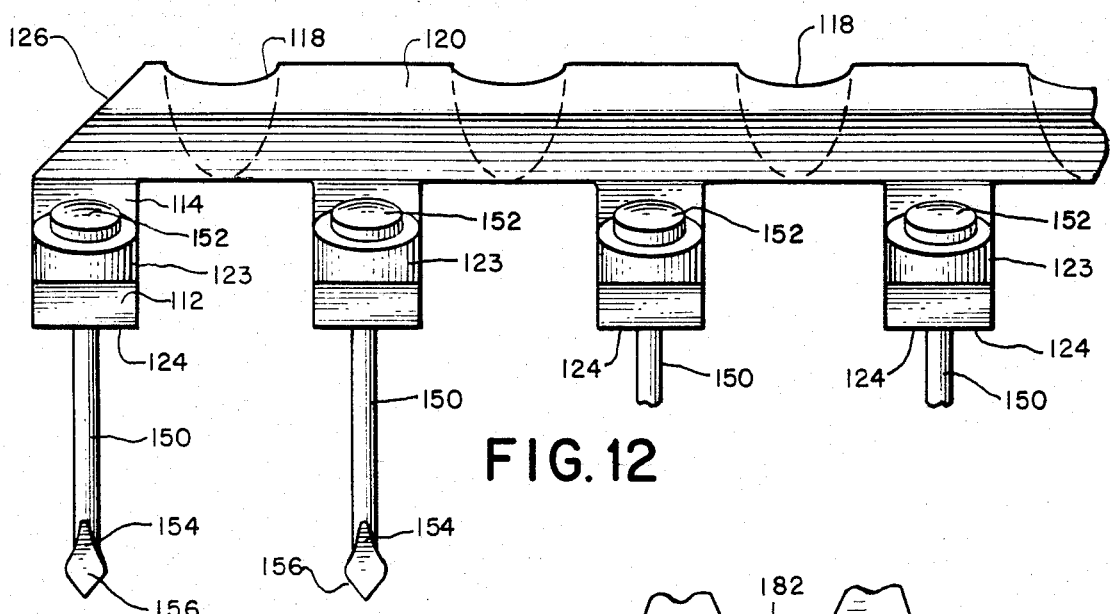
FIG. 12 is a side elevational view of a portion of the pin harness of FIG. 10.
Figure 13:
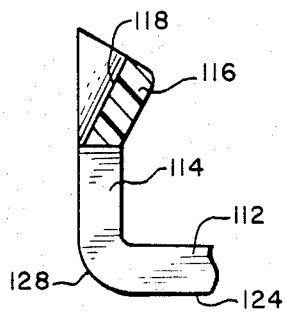
FIG. 13 is a sectional view taken along line 13—13 of FIG. 11.

Turning now to FIGS. 10 through 19, a second preferred embodiment is there illustrated. This second preferred embodiment 100 includes two pin harnesses 110. The relationship between these two pin harnesses 110 in the assembled configuration is shown in FIG. 10. FIGS. 11 through 13 show various additional views of one of the pin harnesses 110 in order further to define its structure. As shown in these figures, each of the pin harnesses 110 includes an array of skin contacting members 112. Each of these skin contacting members 112 is shaped as an elongated, finger-like projection which is mounted to a respective upright member 114. Each of the upright members is in turn mounted to a longitudinal rail 116 which extends across the plurality of the skin contacting members 112. The members 112, 114 and the rail 116 cooperate to form a plurality of apertures 120 therebetween. As best shown in FIG. 12, the rail 116 is maintained above the level of the skin, and the apertures 120 allow free drainage of fluids from the skin wound. In addition, the rail 116 defines a spaced plurality of recesses 118 which serve further to enhance drainage from the skin wound. As best shown in FIG. 12, each end 126 of each of the rails 116 is preferably beveled to facilitate assembly of the skin closure device. Each of the skin contacting members 112 defines a respective pin guide 122 which terminates at its upper end in a boss 123. As best shown in FIG. 10, each of the skin contacting members 112 defines a respective skin contacting surface 124 along its underside surface. The innermost surface of each of the skin contacting members 112 is provided with a radius of curvature 128 to allow for skin eversion adjacent the skin wound.

In this preferred embodiment, the pin guides 122 are spaced such that five pin guides 122 are provided per inch on each pin harness 110. A preferred range for the pin guide spacing is between 3 and 8 pin guides 122 per inch. Simply by way of illustration and not by way of limitation, each of the radiused portions 128 is in this preferred embodiment provided with a radius of curvature of 0.035 inches. Preferably, the pin guides 122 are sized to receive the respective pins in a sliding fit so as to orient the pins properly for penetration of the skin. The angle of the pin guides with respect to the perpendicular to the skin surface can vary within the range of about 0 degrees to about 35 degrees. Within this range, the preferred angle of the pin guides 122 with respect to the perpendicular is about 15 degrees to about 30 degrees. In the presently preferred embodiment, a pin guide angle of about 20 degrees with respect to the perpendicular is considered optimum.

Each of the skin contacting surfaces 124 of the pin harnesses 110 is provided with an adhesive layer 140. Preferably, this adhesive layer 140 extends both around the lower portion of the pin guides 122 as well as to a point partially up the radiused portions 128. Preferably, this adhesive layer is precoated onto the skin contacting surfaces 124 during manufacture.

A wide variety of skin adhesives are suitable for use with the present invention. However, in the presently preferred embodiment the adhesive layer 140 is formed of a skin adhesive distributed by Dow Corning as Adhesive No. 355. This adhesive is a solution of 18.5 percent by weight of dimethylpolysiloxane in trichlorotrifluoroethane (Freon). Of course, this example of a preferred adhesive is provided merely by way of illustration and not of limitation.

Figure 18:
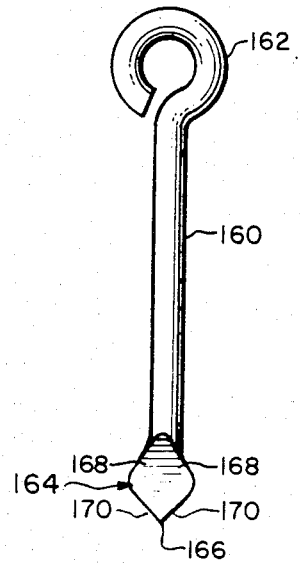
FIG. 18 is an enlarged view of an alternative embodiment of a pin suitable for use in the device of FIG. 10.
Figure 19:
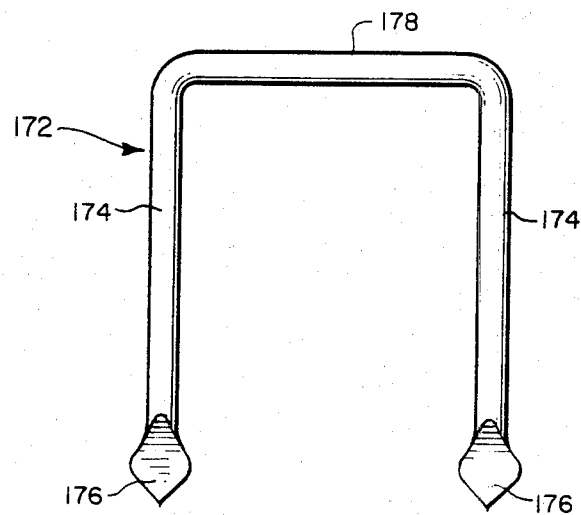
FIG. 19 is an enlarged view of a second alternative embodiment of a pin suitable for use in the device of FIG. 10 or the device of FIG. 20.

As shown in FIG. 10, the skin closure device 100 also includes two sets of pins 150. Each of these pins 150 is provided with an enlarged head 152 as well as with a point 154 which defines a knife-like cutting edge 156. The nature of the points 154 is best shown in FIGS. 18 and 19, which disclose two alternate embodiments of the pin 150. In FIG. 18, the pin 160 is provided with a looped end section 162 and a point 164 which defines an apex 166. In addition, the point 164 defines two enlarged shoulders 168, and a knife-like cutting edge 170 which extends along the sides of the shoulders 168 to the apex 166.

The pin shown in FIG. 19 is yet another alternative embodiment 172 which includes two pin shafts 174, each of which defines a respective point 176 of the type described above. A pin shank 178 connects the two shafts 174 together such that the two shafts 174 form a unit. This embodiment 172 provides the advantage of rapid pin insertion and removal. Simple finger pressure is sufficient to insert the pin 172 easily due to the area and spacing of the shank 178. In each of the pins 150, 160, 172, the angle defined by the cutting edges 156, 170 is preferably about 60 degrees.

By way of example only, the pins can be made of type 316 stainless steel. Of course, other metals or plastic materials of suitable mechanical properties can be substituted. Merely by way of example, in the preferred embodiments discussed above, the shaft of each of the pins is about 0.021 inches in diameter, and the diameter of the pin guides is about 0.0212 inches in diameter. These dimensions provide a close fit of the pins in the pin guides in order to orient the pins properly. In each case, both the heads 152, 162, 178 and the points 154, 164, 176 of the pins are enlarged so as to prevent the pins from escaping from the pin guides 122. In this way, each pin is slidably captured within its pin guide and cannot readily be lost or removed from the pin harness. In this preferred embodiment, the presently preferred length of the pin 150 from the tip of the point 154 to the underside of the head 152 is about 0.311 inches. An alternative embodiment provides a pin 150 with a length of about 0.230 inches.

Figure 14:
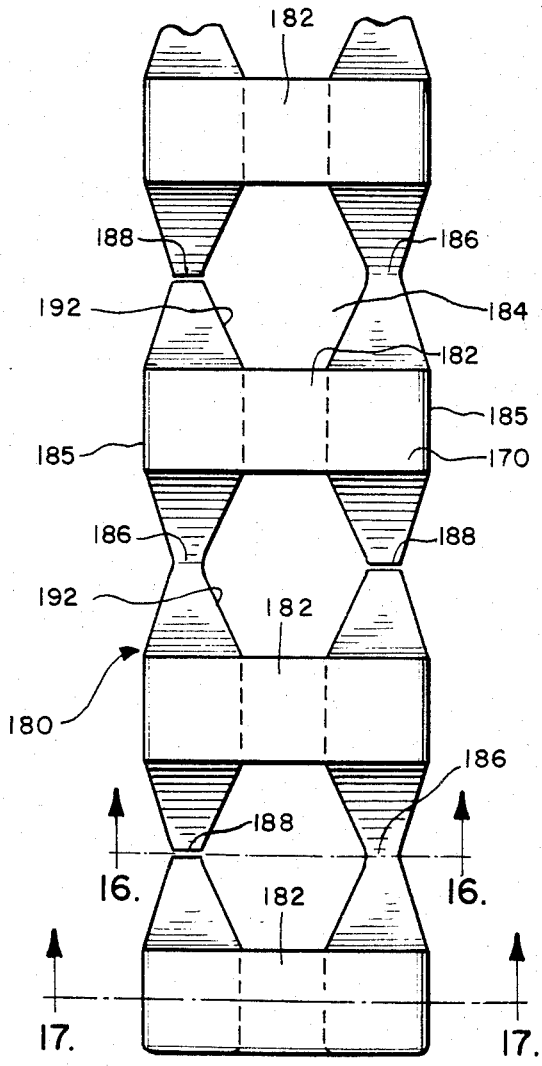
FIG. 14 is a top plan view of a portion of the housing of the embodiment of FIG. 10.
Figure 15:
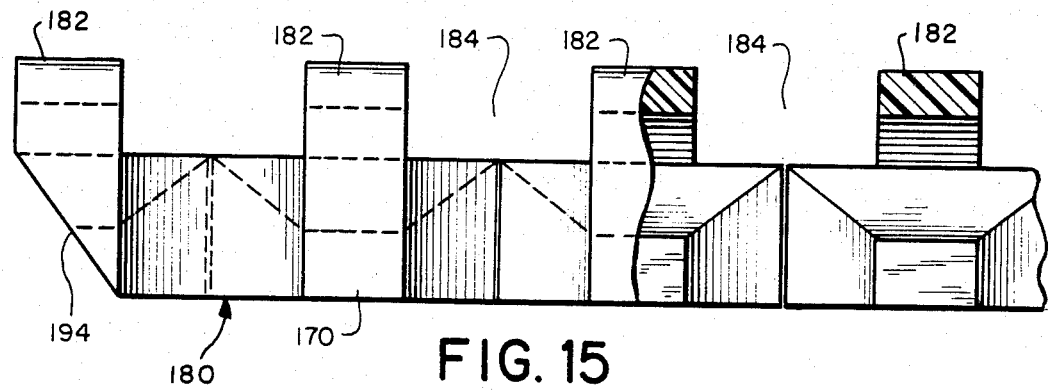
FIG. 15 is a side elevational view of a portion of the housing of FIG. 14.
Figure 16:
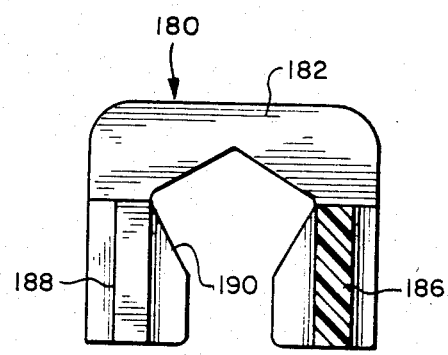
FIG. 16 is a sectional view taken along line 16—16 of FIG. 14.
Figure 17:
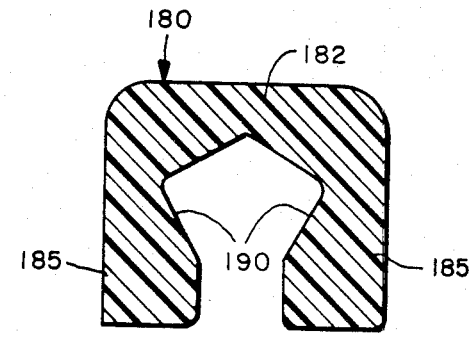
FIG. 17 is a sectional view taken along line 17—17 of FIG. 14.

Turning now to FIGS. 14 through 16, the skin closure device 100 also includes a housing 180. This housing 180 is an elongated member which defines a U-shaped cross section. The housing 180 is made up of a plurality of bridge sections 182 which interconnect two opposed side skirts or sidewalls 185. An array of cross slots 184 are positioned between the bridge portions 182 to intersect the channel 190 defined between the sidewalls 185. These cross slots 184 provide openings or apertures 192 which facilitate the drainage of fluids from the skin wound. As best shown in FIG. 14, each of the sidewalls 185 defines alternately positioned narrowed regions 186 and severed regions 188. When the housing 180 is bent laterally in the plane of FIG. 14, the severed regions 188 open and the narrowed regions 186 bend to allow the entire housing 180 to bend laterally. Preferably, the housing 180 is substantially more rigid to bending in a plane perpendicular to the plane of FIG. 14 than in the plane of FIG. 14. Preferably, both ends 194 of the housing 180 are beveled to facilitate assembly of the skin closure device.

In the preferred embodiment 100 of FIGS. 10 through 19, the pin harnesses 110 and the housing 180 are preferably formed of a high density ethylene hexene-1 copolymer such as the material marketed by Phillips Chemical Company, Battlesfield, Okla. as Marlex type HHM 5502. This material has been found to provide excellent properties in terms of minimum skin reaction and optimum rigidity. The flexibility of this material is temperature dependent, and it has been found to be suitable rigid when the skin closure device 100 is being installed adjacent the skin wound and yet to conform properly to the contour of the skin wound as the skin closure device warms to skin temperature. Preferably, the pin harnesses 110 and the housing 180 are injection-molded and the pin guides 122 are cored. It should be understood that it is not essential in all preferred embodiments that the pin guides 122 be circular in cross section; square pin guides or pin guides of other cross-sectional shape can be substituted. The severed regions 188 in the housing 180 can be formed either by injection molding or by a cutting operation subsequent to injection molding.

The pins 150 of the preferred embodiment described above are preferably first formed with a cold forged head and a standard conical point, and are then assembled in the respective pin guides 122. The point 154 which defines with the cutting edges 156 is then formed in a three-step cold forging operation. The first step is a cutting step to trim off the pin at the desired length. This cutting operation is performed in a first station of a suitable metal forming machine. The second step is to coin the points at a second station of the metal forming machine to a paddle shape having a thickness in the range of about 0.002 inches to about 0.007 inches. Then, the point 154 is cut in a third station to a suitable diamond shape. This cutting operation creates the cutting edges 156. By the process described above, the points 154 can be formed in the pins 150 only after the pins 150 have been inserted in the pin guides 122. In this way, the pins 150 are captured securely within the pin guides 122. Preferably, the stainless steel from which the pins 150 are formed is work hardened to a tensile strength of between 210,000 and 230,000 psi.

Preferably, the skin closure device 100 (including the pin harnesses 110, the adhesive layer 140, the pins 150, and the housing 180) is packaged in a suitable material along with a pin-pushing device formed of Marlex as described above and defining a recessed end sized to fit over the heads 152 of the pins 150. Of course, other types of pin pushing devices, such as forceps-like devices adapted to insert a number of pins at once, can also be used.

These packages also preferably include a quantity of a suitable adhesive. In the preferred embodiment, this adhesive is contained in a glass bottle having a permeable neoprene applicator. In the presently preferred embodiment, an adhesive of the type described above is used. However, in order to provide reduced drying times, the Type 355 Dow Corning adhesive is allowed partially to evaporate before the glass bottle is sealed. In the presently preferred embodiment, 11 cc of Type 355 adhesive is allowed to evaporate down to about 6 cc before the bottle is sealed.

Once the package has been assembled in a clean room in accordance with the regulations of 21 CFR820, it is then preferably sterilized. This can be done by placing a large number of the packages near a Cobalt 60 source of gamma radiation. Preferably, the packages are rotated within a radiation chamber until a dosage of at least 2.5 mega rads is obtained. In this way, the entire skin closure device along with its adhesive is completely sterilized.

The skin closure device 100 described above in conjunction with FIGS. 10 through 19 can be used in the manner of the preferred embodiment of FIGS. 5 to 9a. Preferably, adhesive from the applicator is applied to the skin on both sides of the skin wound. Then the skin contacting surfaces 124 of the pin harness 110 are adhesively bonded to the skin in the desired position and the pins 150 are then pushed into the skin. Preferably, the epidermis is adhesively secured to the pin harnesses at points closely adjacent to the marginal edge of the skin wound. In order to obtain optimum results, this region of adhesive bonding should extend to within 0.5 millimeters of the skin wound.

As described above, the skin closure device 100 can either be applied to unbroken skin prior to the formation of a surgical incision, or alternately it can be applied to the marginal edges of the skin wound after the skin wound has been formed. In either case, the housing 180 is used to approximate the rails 116 of the pin harnesses 110 in order to close the skin wound quickly, efficiently and precisely. Generally, no occlusive dressing is needed.

The preferred embodiment 100 described above provides a number of important advantages. Since the skin contacting surfaces 124 are bonded by the adhesive layer 140 to the epithelium at points closely adjacent to the marginal edge of the skin wound, the skin contacting members 112 serve to bring together and align the epithelium layers precisely. Furthermore, the pins 150 are dimensioned such that the points 154 mechanically engage the dermis. The broad surfaces of the points 154 serve to enhance this mechanical engagement. When the housing 180 is used to bring the points 154 of the pins 150 together, the pins 150 serve to mechanically engage the dermis and to cause the marginal edges of the dermis adjacent the wound to come together in proper alignment. In this way, the skin closure device 100 serves automatically and reliably to align both the epithelium layer and the dermis in precise, edge-to-edge contact and alignment. In this way, healing of the skin wound is facilitated and the formation of scar tissue at the skin wound is minimized.

Furthermore, the embodiment of FIGS. 10 through 19 provides pins 150 which are slidable with respect to the pin harnesses 110, yet which are securely captured in the pin guides 122. This structure allows individual pins 150 to be removed from the skin if desired, yet substantially prevents the loss of individual pins. If desired, recesses can be formed in the underside of the pin guides 122 to receive the pin points 154.

Yet another advantage is that the adhesive layer 140 extends adjacent to and around the pins 150. The adhesive layer 140 operates to immobilize the epithelium layer of the skin around the pins 150 in order to minimize relative motion therebetween. Such relative motion can result in the formation of undesirable scar tissue. The layer of adhesive 140 around the pins 150 further serves to seal the opening in the epithelium layer made by the pins 150 in order to reduce infection and the introduction of foreign material into the epithelium.

Figure 20:
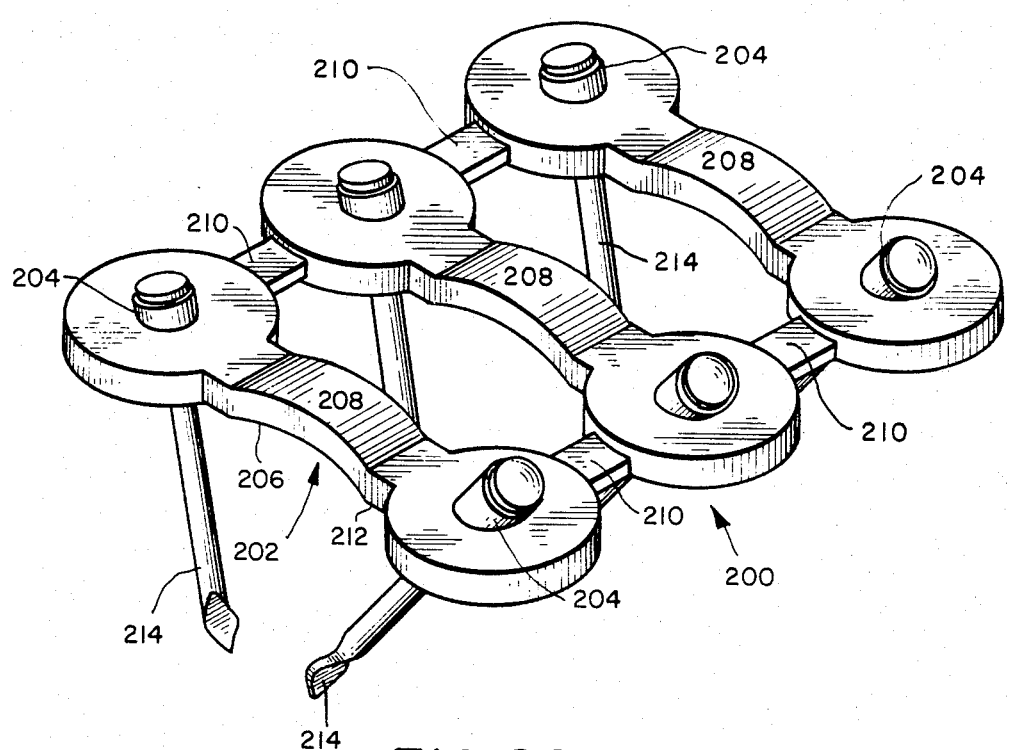
FIG. 20 is a perspective view of a third preferred embodiment of a novel skin closure device.

Turning now to FIG. 20, a third preferred embodiment comprises a plurality of staples 200. Each of the staples 200 is formed of a bridge member 202 which defines two opposed pin guides 204 and an intermediate portion 208 which interconnects the pin guides 204. The underside of the pin guides 204 and the intermediate portion 208 defines a skin contacting surface 206. Adjacent staples 200 are interconnected by means of two side strips 210 which can easily be severed as desired. A layer of a suitable skin adhesive 212 is provided on the entire skin contacting surface 206 (including the underside of the bridge member 202) to form a secure bond between the skin contacting surface 206 and the epithelium on either side of a skin wound. Two pins 214 are captured in and guided by respective ones of the pin guides 204. In general, the details of construction with regard to materials and the shapes of the pins 214 are similar to those described above in conjunction with the skin closure device 100.

The staple 200 is used by first severing the side strips 210 as desired to obtain the desired number of adjacent staples 200. Then the skin contacting surface 206 is adhesively bonded to the skin to bridge a skin wound, using adhesive techniques similar to those described above in conjunction with the skin closure device 100. Then the pins 214 are pushed into the skin, guided by the pin guides 204.

The staple 200 does not provide the advantages of the two preferred embodiments described above with regard to speed of wound closure. However, this embodiment of the invention does provide many of the advantages described above in conjunction with the skin closure device 100. For example, the staple 200 combines the use of an adhesive layer 212 immediately adjacent the marginal edge of the epithelium layer at the skin wound with pins 214 positioned to mechanically engage the dermis adjacent the skin wound in order to bring these two important skin layers together in proper alignment to facilitate healing of the skin wound and to minimize scar formation. This embodiment also provides the advantages describes above with regard to the captured pins, the use of adhesive at the pin sites to immobilize the epithelium adjacent the pins, and the use of spade-shaped pin points to improve mechanical engagement between the pins and the dermis.

Figure 21:
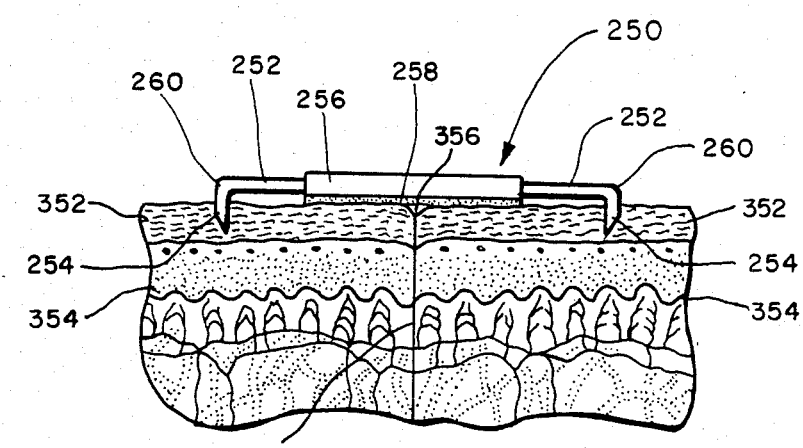
FIG. 21 is a sectional view of a fourth preferred embodiment of a novel skin closure device during an initial stage of insertion across a wound.
Figure 22:
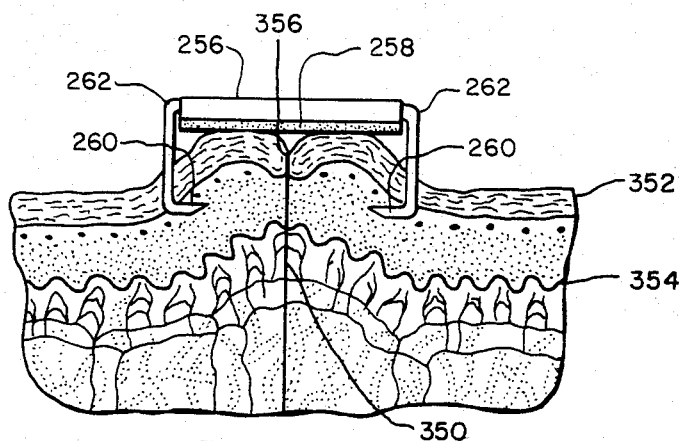
FIG. 22 is a sectional view of the embodiment of FIG. 21 as fully inserted.

Turning now to FIGS. 21 and 22, a fourth preferred embodiment comprises a staple 250 which includes two opposed staple members 252, each of which defines a respective point 254. These two staple members 254 protrude from opposite sides of a rigid staple bridge 256 which interconnects the two staple members 252. The underside of the staple bridge 256 is provided with an adhesive layer 258 of the type described above. Prior to insertion of the staple 250, each of the staple members 252 is provided with a first bend 260. During insertion, the skin is everted, and second bends 262 are formed in the two staple members 252 to configure the staple 250 as shown in FIG. 22. In this configuration, the staple members 252 mechanically engage the dermis in order to align the marginal edges of the dermis on opposed sides of the skin wound with one another and to hold them together. Furthermore, the adhesive layer 258 on the staple bridge 256 engages, aligns and holds together the marginal edges of the epithelium adjacent the skin wound. In this way, both the epithelium and the dermis layers are properly aligned and held together to facilitate healing and to reduce the formation of scar tissue. In many applications, the staple 250 provides reduced precision of alignment of skin layers as compared to the preferred embodiments described above.

Figure 23:
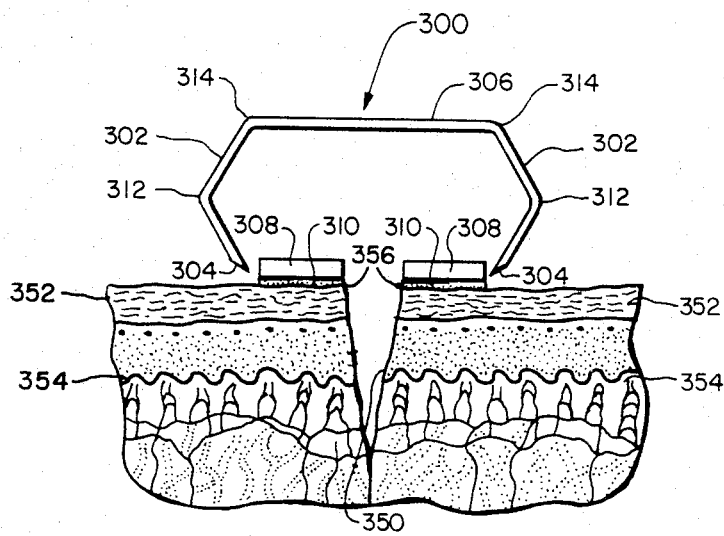
FIG. 23 is a sectional view of a fifth preferred embodiment of a novel skin closure device during an initial stage of insertion across a wound.
Figure 24:
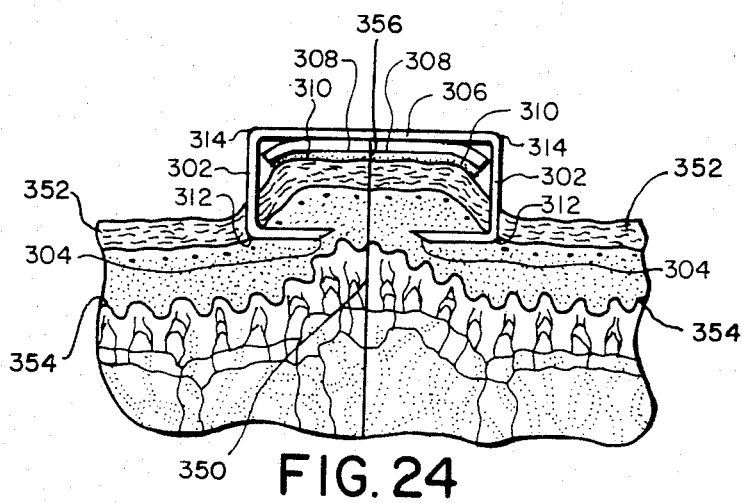
FIG. 24 is a sectional view of the embodiment of FIG. 23 as fully inserted.

Turning now to FIGS. 23 and 24, a fifth preferred embodiment comprises a staple 300. The staple 300 is made up of two opposed staple members 302, each of which defines a respective staple point 304. The two staple members 302 are integrally formed with and interconnected by a rigid staple bridge 306. Two adhesive members 308 are each provided with an adhesive layer 310 of the type described above. In use, the two adhesive members 308 are first adhesively bonded to the marginal edges of the epithelium adjacent the skin wound. The staple members 302 are each provided with first and second bends 312 and 314. Then the staple members 302 are forced into the skin and the second bend 314 is made more acute until the staple bridge 306 captures the adhesive members 308 against the epithelium. In this preferred embodiment, the staple members 302 cooperate with the adhesive members 308 to force the adhesive members 308 together. In a manner similar to that of the staple 250 of FIGS. 21 and 22, the staple members 302 mechanically engage the dermis and the adhesive members 308 adhesively engage the epidermis at points closely adjacent to the marginal edges of the skin wound. In this way, both the epidermis and the dermis layers on either side of the skin wound are properly aligned and held together in order to facilitate healing and to minimize the formation of scar tissue.

From the foregoing, it should be apparent that a variety of skin closure devices have been disclosed which operate to align and approximate both superficial and internal layers of the skin in order to minimize the formation of scar tissue. Of course, a wide variety of changes and modifications to the preferred embodiments described above will be apparent to those skilled in the art. For example, the housing 180 can be replaced with a clamp such as a spring clamp, or it can be designed to snap on and off of the pin harnesses 110. Materials, dimensions, proportions, and shapes can all be modified as desired for individual applications. For example, elements such as the pin harnesses 110 and the housing 180 can be formed of aluminum or stainless steel.

I claim:

1. A skin closure device for closing a skin wound which defines first and second wound margins separated by a denuded region, said device comprising:
   first and second attachment members;
   means for adhesively securing the first and second attachment members to the skin alongside the first and second wound margins, respectively;
   means for mechanically securing the first and second attachment members to the skin alongside the first and second wound margins; and
   means for interconnecting the first and second attachment members across the wound to adjustably control the separation therebetween through a range of at least 0.5 inches in order to to allow said separation to be reduced gradually and progressively in order to close the denuded region gradually;
   said means for adhesively securing and said means for mechanically securing configured such that the attachment members can be adhesively secured to the skin prior to being mechanically secured to the skin.

2. The invention of claim 1 wherein the interconnecting means comprises a deformable clip.

3. The invention of claim 1 wherein the interconnecting means comprises a spring clip.

4. The invention of claim 1 wherein the interconnecting means comprises:
   a strap secured to the first attachment member; and
   means, mounted on the second attachment member, for adjustably securing the strap to the second attachment member at any of a plurality of locations along the strap.

5. The invention of claim 4 wherein the securing means comprises a ratchet adapted to engage the strap and to allow the strap to be moved only to shorten the separation between the two attachment members.

6. The invention of claim 1 wherein the interconnecting means is effective to maintain a force tending to reduce the separation between the two attachment members for a range of separations of the two attachment members.

7. The invention of claim 1 wherein the mechanically securing means comprises first and second sets of pins positioned to slide with respect to and extend from the respective attachment members into the skin.

8. A method for closing a skin wound which defines first and second wound margins separated by a denuded region, said method comprising:
   providing a skin closure device comprising first and second attachment members and means for interconnecting the first and second attachment members across the wound to adjustably control the separation therebetween;
   adhesively securing the first and second attachment members to the skin alongside the first and second wound margins, respectively;
   mechanically securing the first and second attachment members to the skin alongside the first and second wound margins, respectively;
   interconnecting the first and second attachment members with the interconnecting means to bias the two attachment members together to tend to close the wound; and then
   gradually and progressively shortening the interconnecting means in order to draw the attachment members together gradually over the course of at least several days in order to close the wound gradually.

9. The invention of claim 8 wherein the interconnecting means comprises a metal clip and wherein the shortening step comprises the step of progressively bending the clip to reduce the effective length of the clip.

10. The invention of claim 8 wherein the interconnecting means comprises a strap extending between the attachment members and wherein the shortening step comprises the step of progressively shortening the effective length of the strap between the attachment members.

11. The invention of claim 10 wherein the interconnecting means further comprises a ratchet adapted to receive and engage the strap, and wherein the progressive shortening step comprises the step of progressively pulling the strap through the ratchet.

12. The invention of claim 8 wherein the interconnecting means comprises a spring clip and spring forces developed by the spring clip drive the shortening step.

13. The invention of claim 8 wherein the mechanically securing step comprises the step of pushing a plurality of pins which extend from the attachment members into the skin.

14. A skin closure device for closing a skin wound which defines first and second wound margins separated by a denuded region, said device comprising:
   first and second attachment members, both of which define a respective adhesively coated underside and a respective plurality of pin guides, said attachment members shaped to adhesively bond to the skin alongside respective ones of the first and second wound margins, said pin guides shaped to remain outside the skin when the attachment members are adhesively bonded to the skin;
   a plurality of pins, each slidably disposed in a respective one of the pin guides to engage the skin mechanically in order mechanically to secure the respective attachment member to the skin; and
   at least one interconnecting member secured between the two attachment members to bias the two attachment members together, said interconnecting member having an effective length which is adjustable through a range of greater than 0.5 inches in order to bias the attachment members together throughout a range of separations as the wound is gradually closed.

15. The invention of claim 14 wherein the interconnecting member comprises a bendable metal clip.

16. The invention of claim 14 wherein the interconnecting means comprises a spring clip.

17. The invention of claim 14 wherein the interconnecting means comprises a strap fixedly secured to the first attachment member and means for adjustably securing the strap to the second attachment member at any one of a plurality of positions along the length of the strap.

18. The invention of claim 17 wherein the securing means comprises a ratchet adapted to engage the strap and to allow the strap to be moved only to shorten the separation between the two attachment members.

19. A skin closure device for closing a skin wound which defines first and second wound margins separated by a denuded region, said device comprising:
   first and second attachment members;
   means for adhesively securing the first and second attachment members to the skin alongside the first and second wound margins, respectively;
   means for mechanically securing the first and second attachment members to the skin alongside the first and second wound margins; and
   means for interconnecting the first and second attachment members across the wound to adjustably control the separation therebetween through a range of at least 0.5 inches in order to to allow said separation to be reduced gradually and progressively in order to close the denuded region gradually;
   said interconnecting means comprising:
   a strap secured to the first attachment member; and
   means, mounted on the second attachment member, for adjustably securing the strap to the second attachment member at any of a plurality of locations along the strap;
   said securing means comprising a ratchet adapted to engage the strap and to allow the strap to be moved only to shorten the separation between the two attachment members.

20. A skin closure device for closing a skin wound which defines first and second wound margins separated by a denuded region, said device comprising:
   first and second attachment members, both of which define a respective adhesively coated underside and a respective plurality of pin guides, said attachment members shaped to adhesively bond to the skin alongside respective ones of the first and second wound margins;
   a plurality of pins, each disposed in a respective one of the pin guides to engage the skin mechanically in order mechanically to secure the respective attachment member to the skin; and
   at least one interconnecting member secured between the two attachment members to bias the two attachment members together, said interconnecting member having an effective length which is adjustable through a range of greater than 0.5 inches in order to bias the attachment members together throughout a range of separations as the wound is gradually closed;
   said interconnecting means comprising a strap fixedly secured to the first attachment member and means for adjustably securing the strap to the second attachment member at any one of a plurality of positions along the length of the strap;
   said securing means comprising a ratchet adapted to engage the strap and to allow the strap to be moved only to shorten the separation between the two attachment members.

* * * * *

UNITED STATES PATENT AND TRADEMARK OFFICE
CERTIFICATE OF CORRECTION

PATENT NO. : 4,535,772
DATED : Aug. 20, 1985
INVENTOR(S) : Joseph C. M. Sheehan

It is certified that error appears in the above-identified patent and that said Letters Patent is hereby corrected as shown below:

IN THE DETAILED DESCRIPTION OF THE PRESENTLY PREFERRED EMBODIMENTS

In column 10, line 9, please delete "strips" and substitute therefor --straps--;

IN THE PRIOR ART SKIN CLOSURE DEVICES

In column 12, line 44, please delete "change" and substitute therefor --chance--;

IN THE SKIN CLOSURE DEVICES RELATED TO THE PRESENT INVENTION

In column 19, line 48, please delete "suitable" and substitute therefor --suitably--;

Signed and Sealed this

Fifteenth Day of December, 1987

Attest:

DONALD J. QUIGG

*Attesting Officer*     *Commissioner of Patents and Trademarks*

UNITED STATES PATENT AND TRADEMARK OFFICE
CERTIFICATE OF CORRECTION

PATENT NO. : 4,535,772

DATED : August 20, 1985

INVENTOR(S) : Joseph C. M. Sheehan

It is certified that error appears in the above-identified patent and that said Letters Patent is hereby corrected as shown below:

IN THE CLAIMS

In Claim 1, (column 23, line 24), please delete "to" (second occurrence);

In Claim 19, (column 25, line 18), please delete "to" (second occurrence).

Signed and Sealed this

Sixteenth Day of February, 1988

Attest:

DONALD J. QUIGG

Attesting Officer

Commissioner of Patents and Trademarks